US007329656B2

(12) United States Patent
Marzabadi et al.

(10) Patent No.: US 7,329,656 B2
(45) Date of Patent: Feb. 12, 2008

(54) ARYLTHIOBENZYLPIPERIDINE DERIVATIVES

(75) Inventors: Mohammad R. Marzabadi, Ridgewood, NJ (US); Yu Jiang, Jersey City, NJ (US); Chien-An Chen, Flushing, NY (US); Kai Lu, Lake Hiawatha, NJ (US); Kim Andersen, Ridgewood, NJ (US)

(73) Assignee: H. Lundbeck A/S, Valby (DK)

( * ) Notice: Subject to any disclaimer, the term of this patent is extended or adjusted under 35 U.S.C. 154(b) by 70 days.

(21) Appl. No.: 11/231,601

(22) Filed: Sep. 21, 2005

(65) Prior Publication Data

US 2006/0079523 A1    Apr. 13, 2006

Related U.S. Application Data

(60) Provisional application No. 60/616,980, filed on Oct. 8, 2004.

(51) Int. Cl.
| | | |
|---|---|---|
| *A61K 31/4545* | (2006.01) | |
| *A61K 31/444* | (2006.01) | |
| *A61K 31/5377* | (2006.01) | |
| *C07D 211/04* | (2006.01) | |
| *C07D 401/04* | (2006.01) | |
| *C07D 413/14* | (2006.01) | |

(52) U.S. Cl. .................. 514/231.5; 514/326; 514/318; 546/193; 546/194; 546/207; 544/124; 544/129

(58) Field of Classification Search ................ 514/318, 514/326; 546/193, 194, 207, 208, 209, 210
See application file for complete search history.

(56) References Cited

U.S. PATENT DOCUMENTS

| 6,503,928 B2 | 1/2003 | Kelly et al. |
| 6,727,264 B1 | 4/2004 | Marzabadi et al. |

FOREIGN PATENT DOCUMENTS

| EP | 1 020 434 | 7/2000 |
| WO | WO 02/094799 | 11/2002 |
| WO | WO 03/004027 | 1/2003 |
| WO | WO 2004/005257 | 1/2004 |
| WO | WO 2004/052848 | 6/2004 |

OTHER PUBLICATIONS

U.S. Appl. No. 10/719,358, Marzabadi et al.
Browning, "Recent developments in the discovery of melanin-concentrating hormone antagonists: novel antiobesity agents", Expert Opinion in Therapeutic Patents, Mar. 2004, 14(3):313-325.
Carpenter & Hertzog, "Melanin-concentrating hormone receptor antagonists as potential antiobesity agents", Expert Opinion in Therapeutic Patents, Nov. 2002, 12(11):1639-1646.
Collins & Kym, "Prospects for obesity treatment: MCH receptor antagonists", Current Opinion in Investigational Drugs, Apr. 2003, 4(4):386-394.
Kowalski & McBriar, "Therapeutic potential of melanin-concentrating hormone-1 receptor antagonists for the treatment of obesity", Expert,Opinion in Investigational Drugs, Sep. 2004, 13(9):1113-1122.
Takekawa, et al., "T-226296: a novel, orally active and selective melanin-concentrating hormone receptor antagonist", European Journal of Pharm., Mar. 2002, 438(3):129-135.

*Primary Examiner*—Rebecca Anderson
*Assistant Examiner*—Yong Chu
(74) *Attorney, Agent, or Firm*—Lundbeck Research USA

(57) ABSTRACT

This invention is directed to Arylthiobenzylpiperidine derivatives which are ligands at the MCH1 receptor. The invention provides a pharmaceutical composition comprising a therapeutically effective amount of a compound of the invention and a pharmaceutically acceptable carrier. This invention also provides a pharmaceutical composition made by admixing a therapeutically effective amount of a compound of the invention and a pharmaceutically acceptable carrier. This invention further provides a process for making a pharmaceutical composition comprising combining a therapeutically effective amount of a compound of the invention and a pharmaceutically acceptable carrier. This invention also provides a method of treating a subject suffering from depression and/or anxiety which comprises administering to the subject a therapeutically effective amount of a compound of the subject invention. This invention also provides a method of treating a subject suffering from obesity which comprises administering to the subject a therapeutically effective amount of a compound of the subject invention.

21 Claims, No Drawings

ARYLTHIOBENZYLPIPERIDINE DERIVATIVES

This application claims the benefit of U.S. Provisional Application No. 60/616,980 filed Oct. 8, 2004, the contents of which are hereby incorporated by reference.

FIELD OF THE INVENTION

The present invention relates to compounds that are ligands at the MCH1 receptor, and as such are useful to treat depression, anxiety or obesity.

BACKGROUND OF THE INVENTION

Throughout this application, various publications are referenced to in full citations. The disclosures of these publications are hereby incorporated by reference into this application to describe more fully the state of the art to which this invention pertains.

Melanin-concentrating hormone (MCH) is a cyclic 19-amino acid peptide produced by neurons in the lateral hypothalamus and zona incerta of the brain. Mammalian MCH is conserved between rat, mouse, and human, exhibiting 100% amino acid homology, and the effects of MCH are mediated through receptors that belong in the rhodopsin superfamily of G protein-coupled receptors. Presently, two receptor subtypes for MCH have been identified in humans, MCH1 and MCH2.

The link between MCH1 and the effects of MCH on feeding was suggested by reports on the phenotype of the MCH1 knockout mice. Independent groups generated knock-out mice with the targeted deletion of the MCH1 receptor. The phenotype of these mice was lean, hyperphagic and hypermetabolic, with increased resistance to diet-induced obesity (D. J. Marsh, et al., *Proc. Natl. Acad. Sci.* 2002, 99, 3240-3245). These observations evidence that MCH1 antagonists are useful to treat obesity.

To further assess the physiological role of the MCH1 receptor, SNAP-7941, a selective MCH1 small molecule antagonist, was evaluated in several animal models (B. Borowsky, et al., *Nature Medicine*, 2002, 8, 825-830). Pharmacological blockade of the MCH1 receptor with SNAP-7941 produced a profile similar to clinically used anti-depressants and anxiolytics in behavioral models of depression and/or anxiety: the rat forced-swim, rat social interaction and guinea pig maternal-separation vocalization tests. These observations evidence that MCH1 antagonists are useful to treat depression and anxiety.

Current treatments for depression, anxiety and obesity are on the market. However, numerous patients do not respond to current treatments. Hence, there remains the need for alternative methods of treatment.

SUMMARY OF THE INVENTION

The objective of the present invention is to provide compounds that are ligands at the MCH1 receptor. The present invention relates to compounds of Formula I.

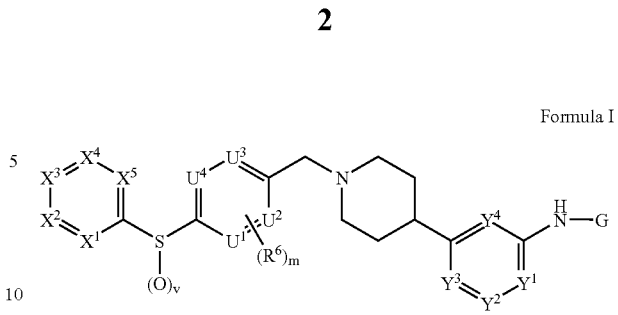

Formula I wherein each $X^1$, $X^2$, $X^3$, $X^4$ and $X^5$ is independently $CR^1$ or N, provided that if one X is N then the remaining X are each $CR^1$;

wherein each $U^1$, $U^2$, $U^3$ and $U^4$ is independently CH or N, provided that if one U is N then the remaining U are each CH;

wherein each $Y^1$, $Y^2$, $Y^3$ and $Y^4$ is independently $CR^7$ or N, provided that if one Y is N then the remaining Y are each $CR^7$;

wherein G is hydrogen or —C(O)D;

wherein D is composed of one of the following moieties

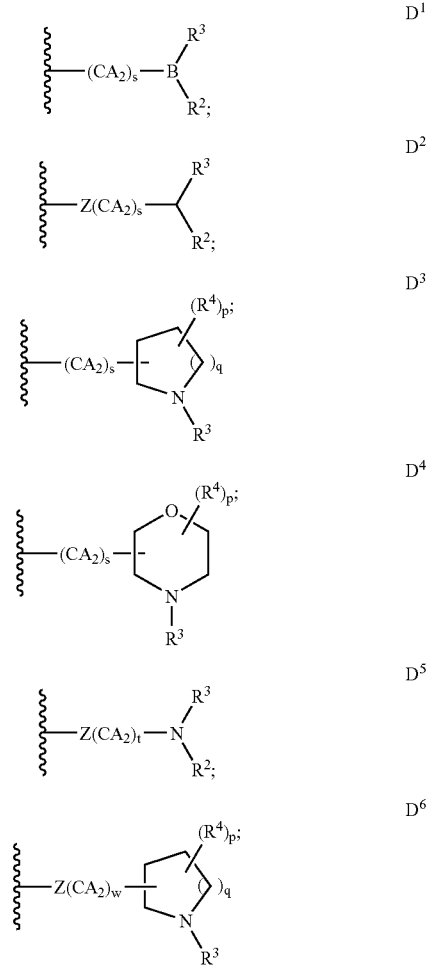

-continued

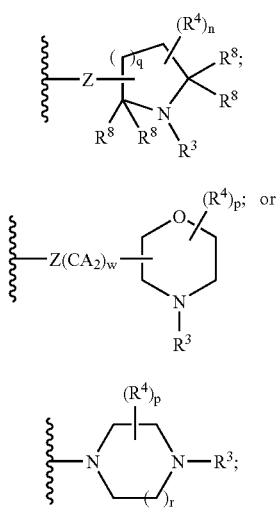

wherein Z is —N(R$^5$) or —O—;

wherein each A is independently H or straight chained or branched C$_1$-C$_4$ alkyl;

wherein B is CH or N;

wherein each R$^1$ is independently H, straight chained or branched C$_1$-C$_7$ alkyl, straight chained or branched C$_1$-C$_7$ fluoroalkyl, straight chained or branched C$_1$-C$_7$ alkoxy, F, Cl, Br or I;

wherein R$^2$ is H or straight chained or branched C$_1$-C$_4$ alkyl;

wherein R$^3$ is H or straight chained or branched C$_1$-C$_4$ alkyl;

or wherein if B is N, then the R$^2$ moiety, B, the R$^3$ moiety and a bond formed between the R$^2$ moiety and the R$^3$ moiety form:

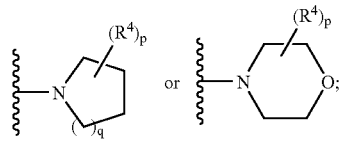

or wherein if B is CH, then the R$^2$ moiety, B, the R$^3$ moiety and a bond formed between the R$^2$ moiety and the R$^3$ moiety form cyclopropyl, cyclobutyl, cyclopentyl or cyclohexyl.

wherein R$^4$ is H, straight chained or branched C$_1$-C$_4$ alkyl, straight chained or branched C$_1$-C$_4$ fluoroalkyl or F;

wherein R$^5$ is H or straight chained or branched C$_1$-C$_4$ alkyl;

wherein each R$^6$ is independently straight chained or branched C$_1$-C$_7$ alkyl, straight chained or branched C$_1$-C$_7$ fluoroalkyl, straight chained or branched C$_1$-C$_7$ alkoxy, F, Cl, Br or I;

wherein each R$^7$ is independently H, straight chained or branched C$_1$-C$_7$ alkyl, straight chained or branched C$_1$-C$_7$ fluoroalkyl, straight chained or branched C$_1$-C$_7$ alkoxy, F, Cl, Br or I;

wherein R$^8$ is H, straight chained or branched C$_1$-C$_4$ alkyl, straight chained or branched C$_1$-C$_4$ fluoroalkyl or F;

wherein m is an integer from 0 to 4 inclusive;

wherein n is an integer from 0 to 2 inclusive;

wherein p is an integer from 0 to 4 inclusive;

wherein q is an integer from 0 to 3 inclusive;

wherein r is 1 or 2;

wherein s is an integer from 0 to 4 inclusive;

wherein t is an integer from 2 to 4 inclusive;

wherein v is an integer from 0 to 2 inclusive; and wherein w is an integer from 1 to 5 inclusive;

or a pharmaceutically acceptable salt thereof.

In separate embodiments of the invention, the compound is selected from one of the specific compounds disclosed in the Experimental Section.

Furthermore, the present invention provides a pharmaceutical composition comprising a therapeutically effective amount of a compound of Formula I and a pharmaceutically acceptable carrier. The present invention also provides a process for making a pharmaceutical composition comprising admixing a compound of Formula I and a pharmaceutically acceptable carrier.

Moreover, the present invention provides a method of treating a subject suffering from depression comprising administering to the subject a therapeutically effective amount of a compound of Formula I. The present invention further provides a method of treating a subject suffering from anxiety comprising administering to the subject a therapeutically effective amount of a compound of Formula I.

DETAILED DESCRIPTION OF THE INVENTION

Definitions

In the present invention, the term "straight chained or branched C$_1$-C$_7$ alkyl" refers to a saturated hydrocarbon having from one to seven carbon atoms inclusive. Examples of such substituents include, but are not limited to, methyl, ethyl, 1-propyl, 2-propyl, 1-butyl, 2-butyl, 2-methyl-2-propyl, 2-methyl-1-propyl and n-heptyl. Similarly, the term "straight chained or branched C$_1$-C$_4$ alkyl" refers to a saturated hydrocarbon having from one to four carbon atoms inclusive.

The term "straight chained or branched C$_1$-C$_7$ fluoroalkyl" refers to a saturated hydrocarbon having from one to seven carbon atoms inclusive substituted with one or more fluorine atoms. Examples of such substituents include, but are not limited to, trifluoromethyl, pentafluoroethyl, 1-fluoroethyl and 1,2-difluoroethyl and 2,3-difluoroheptyl. Similarly, the term "straight chained or branched C$_1$-C$_4$ fluoroalkyl" refers to a saturated hydrocarbon having from one to four carbon atoms inclusive substituted with one or more fluorine atoms per carbon atom.

The term "straight chained or branched C$_1$-C$_7$ alkoxy" refers to a saturated alkoxy group having from one to seven carbon atoms inclusive with the open valency on the oxygen. Examples of such substituents include, but are not limited to, methoxy, ethoxy, n-butoxy, t-butoxy and n-heptyloxy.

The specific compounds disclosed in the present invention are identified by their IUPAC names. The names of the compounds were generated using the program Chemistry 4-D Draw Nomenclator™ Database (Version 7.01c, ChemInnovation Software, Inc.). According to ChemInnovation Software Inc., Nomenclator™ automatically assigns systematic names to organic structures according to IUPAC nomenclature rules. Accordingly, this application discloses the Arylthiobenzylpiperidine derivatives encompassed by Formula I in accordance with IUPAC nomenclature rules.

For illustrative purposes, and without limiting the invention, the compound of example 1k has the following structure:

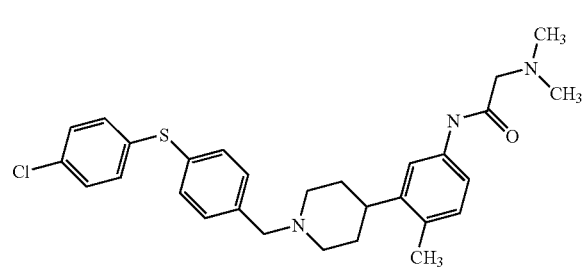

This compound is constructed from Formula I wherein each $X^1$, $X^2$, $X^3$, $X^4$ and $X^5$ is $CR^1$; wherein each $U^1$, $U^2$, $U^3$ and $U^4$ is CH; wherein each $R^1$ is independently H or Cl; wherein v is 0; wherein m is 0; wherein each $Y^1$, $Y^2$, $Y^3$ and $Y^4$ is $CR^7$; wherein each $R^7$ is independently H or methyl; wherein G is —C(O)D; wherein D is $D^1$; wherein s is 1; wherein each A is H; wherein B is N; wherein $R^2$ is methyl and wherein $R^3$ is methyl.

Additionally, the invention further provides certain embodiments of the present invention that are described below.

In one embodiment of the invention of Formula I, the compound has the structure:

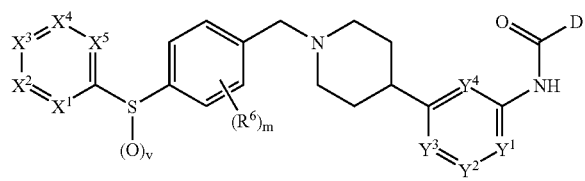

In one embodiment, m is 0 or 1, and $R^6$ is methyl, F or Cl.

In another embodiment, each $X^1$, $X^2$, $X^3$, $X^4$ and $X^5$ is $CR^1$, and each $Y^1$, $Y^2$, $Y^3$ and $Y^4$ is $CR^7$.

In another embodiment, each $R^1$ is independently H, methyl, F or Cl, and each $R^7$ is independently H, F or methyl.

In another embodiment, D is

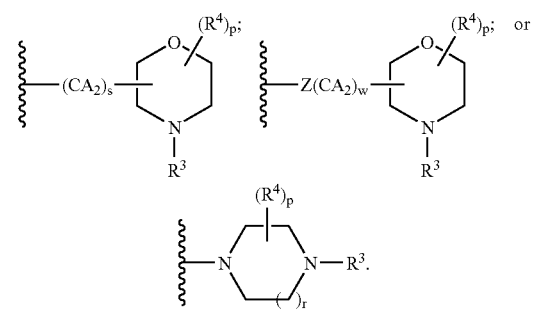

In another embodiment, p is 0 and $R_3$ is H or methyl.

In another embodiment, D is

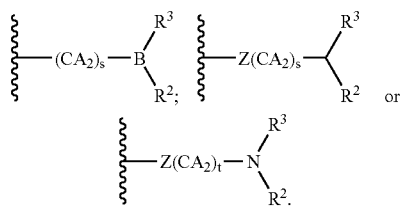

In another embodiment, D is

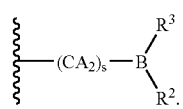

In another embodiment, if B is N, then the $R^2$ moiety, B, the $R^3$ moiety and the bond formed between the $R^2$ moiety and the $R^3$ moiety form:

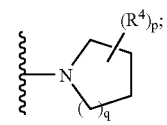

or wherein B is CH then the $R^2$ moiety, B, the $R^3$ moiety and the bond formed between the $R^2$ moiety and the $R^3$ moiety form cyclopropyl, cyclobutyl, cyclopentyl or cyclohexyl.

In another embodiment, B is N, and $R^2$ and $R^3$ are each independently H, methyl or ethyl.

In another embodiment, s is 1 or 2.

In another embodiment, $R^2$ and $R^3$ are each independently H, methyl or ethyl and B is CH.

In another embodiment, each A is independently H, methyl or ethyl; s is 0 or 1; and m is 0.

In another embodiment, D is

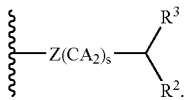

In another embodiment, each A is independently H, methyl or ethyl; Z is O; s is 0 or 1; and m is 0.

In another embodiment, $R^2$ and $R^3$ are independently H, methyl or ethyl.

In another embodiment, D is

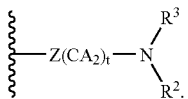

In another embodiment, the $R^2$ moiety, N, the $R^3$ moiety and the bond formed between the $R^2$ moiety and the $R^3$ moiety form:

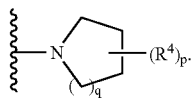

In another embodiment, $R^2$ and $R^3$ are independently H, methyl or ethyl.

In another embodiment, D is

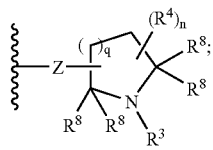

n is 0 and $R^3$ is H or methyl.

In another embodiment, D is

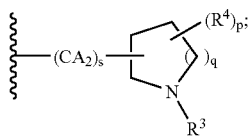

p is 0 and $R^3$ is H or methyl.

In another embodiment, s is 0 or 1.

In another embodiment, D is

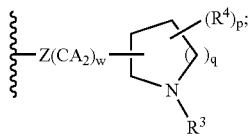

p is 0 and $R^3$ is H or methyl.

In one embodiment, each $U^1$, $U^2$, $U^3$ and $U^4$ is CH; and G is hydrogen.

In one embodiment, m is 0 or 1 and $R^6$ is methyl, F or Cl.

In one embodiment, each $X^1$, $X^2$, $X^3$, $X^4$ and $X^5$ is $CR^1$, and each $Y^1$, $Y^2$, $Y^3$ and $Y^4$ is $CR^7$.

In one embodiment, each $R^1$ is independently H, methyl, F or Cl; and each $R^7$ is independently H, F or methyl.

In one embodiment, each $Y^1$, $Y^2$, $Y^3$ and $Y^4$ is $CR^7$ and G is —C(O)D.

In one embodiment, one U is N.

In one embodiment, m is 0 or 1 and $R^6$ is methyl, F or Cl.

In one embodiment, D is

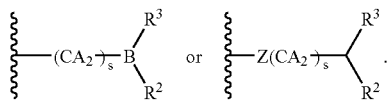

In one embodiment, Z is O.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in S. M. Berge, et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, madelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, e.g., chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compound of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York 1981. Optically active compounds were also be prepared from optically active starting materials.

The invention also encompasses prodrugs of the present compounds, which on administration undergo chemical conversion by metabolic processes before becoming pharmacologically active substances. In general, such prodrugs will be functional derivatives of the compounds of Formula I which are readily convertible in vivo into the required compound of Formula I. Conventional procedures for the selection and preparation of suitable prodrug derivatives are described in Design of Prodrugs, ed. H. Bundgaard, Elsevier, 1985.

Pharmaceutical Compositions

The present invention further provides a pharmaceutical composition comprising a therapeutically effective amount of a compound of Formula I and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of Formula I and a pharmaceutically acceptable carrier. In an embodiment of the present invention the compound utilized in the aforementioned process is one of the specific compounds disclosed in the Experimental Section.

The compounds of this invention are generally utilized as the free substance or as a pharmaceutically acceptable salt thereof. One example is an acid addition salt of a compound having the utility of a free base. When a compound of Formula I contains a free base such salts are prepared in a conventional manner by treating a solution or suspension of a free base of Formula I with a molar equivalent of a pharmaceutically acceptable acid. Representative examples of suitable organic and inorganic acids are described above.

For parenteral administration, solutions of the compounds of Formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of Formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of Formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit.

If a liquid carrier is used, the preparation may be in the form of a syrup, emulsion, soft gelatin capsule or sterile injectable liquid such as an aqueous or non-aqueous liquid suspension or solution.

Treatment of Disorders

As mentioned above, the compounds of Formula I are ligands at the MCH1 receptor. The present invention provides a method of treating a subject suffering from depression and/or anxiety which comprises administering to the subject a therapeutically effective amount of a compound of this invention. This invention further provides a method of treating a subject suffering from major depression and/or anxiety which comprises administering to the subject a therapeutically effective amount of a compound of this invention. This invention also provides a method of treating a subject suffering from obesity which comprises administering to the subject a therapeutically effective amount of a compound of this invention. In an embodiment of this invention, the subject is a human being.

The invention will be better understood from the Experimental Details which follow. However, one skilled in the art will readily appreciate that the specific methods and results discussed therein are merely illustrative of the invention as described more fully in the claims which follow thereafter. Furthermore, the variables depicted in Schemes 1-12 are consistent with the variables recited in the Summary of the Invention. For clarity purposes, the variables $X^1$, $X^2$, $X^3$, $X^4$ and $X^5$ are designated as variable X in the experimental schemes. The variables $U^1$, $U^2$, $U^3$ and $U^4$ are designated as variable U in the experimental schemes. Moreover, the variables $Y^1$, $Y^2$, $Y^3$ and $Y^4$ are designated as variable Y in the experimental schemes.

In the Experimental Section, standard acronyms are used. Examples of such acronyms include AIBN (2,2'-Azobisisobutyronitrile); DMF (N,N-Dimethylformamide); DMSO (Dimethylsulfoxide); NBS (N-Bromosuccinimide); MTBE (methyl t-butyl ether); HATU (O-(7-Azabenzotriazol-1-yl)-N,N,N',N'-tetramethyluronium hexafluorophosphate); mCPBA (3-chloroperoxybenzoic acid); CbzCl (Benzyl chloroformate); and BOC (tert-butoxycarbonyl). Furthermore in certain instances, the methods of preparing the compounds of the invention are described generally by referring to representative reagents such as bases or solvents. The particular reagent identified is representative but is not inclusive or does not limit the invention in any way. For example, representative bases include but are not limited to $K_2CO_3$, $Et_3N$ or DIPEA (Diisopropylethylamine).

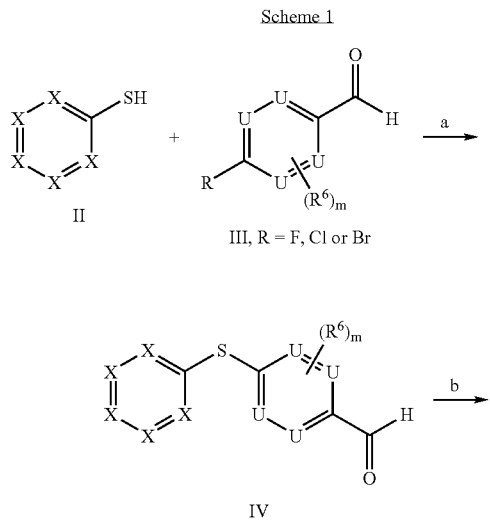

Scheme 1

III, R = F, Cl or Br

IV

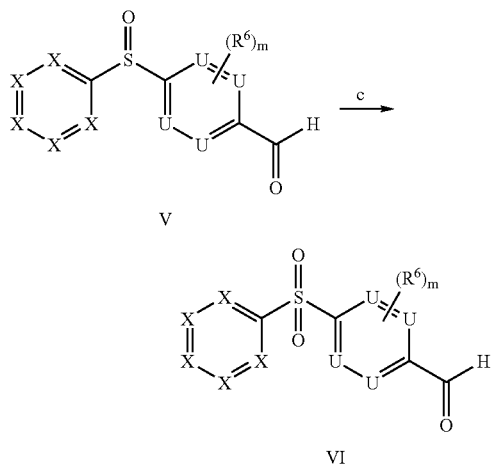

-continued

V

VI (a) $K_2CO_3$/DMF or DMSO/reflux, 6 h or microwave/250° C., 5 min or NaH/DMF.
(b) mCPBA (1 eq)/$CH_2Cl_2$/0° C., 15 min. (c) mCPBA (1 eq)/$CH_2Cl_2$/0° C., 15 min.

The aldehydes of Formula IV, V and VI, which are used as starting materials in Scheme 8, are either available from commercial sources or prepared as shown in Scheme 1. The aldehydes of Formula IV are prepared via aromatic nucleophilic reaction of thiophenols II and activated 4-halo-benzaldehydes III in the presence of base under reflux or microwave conditions. Alternatively, the aldehydes of Formula IV may be prepared via Ullmann type reactions (Kondo, T. et al, *Chem. Rev.* 2000, 100, 3205-3220 and the references cited therein). The corresponding sulfoxides V and sulfones VI are prepared via sequential oxidations of IV by mCPBA as shown in Scheme 1. Alternatively, the aldehydes of Formula VI may be synthesized via a sequence of protection, oxidation and deprotection of the aldehyde IV by using standard conditions.

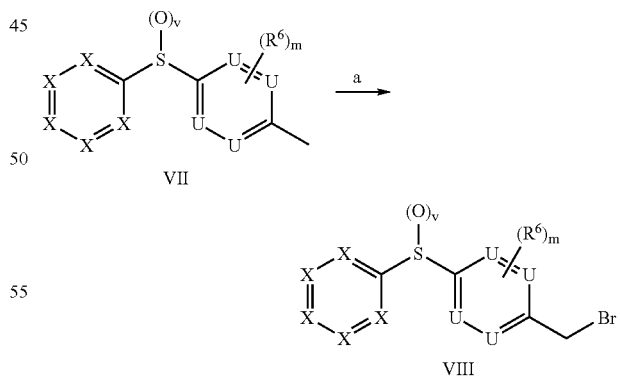

Scheme 2

VII

VIII (a) NBS/AIBN/$CCl_4$/refluxing, 24 h

The benzylbromides of Formula VIII, which are used as starting materials in Scheme 9, are either available from commercial sources or prepared via bromination reactions from the corresponding 4-methyl-benzenes VII in the presence of NBS under reflux as shown in Scheme 2.

Scheme 3

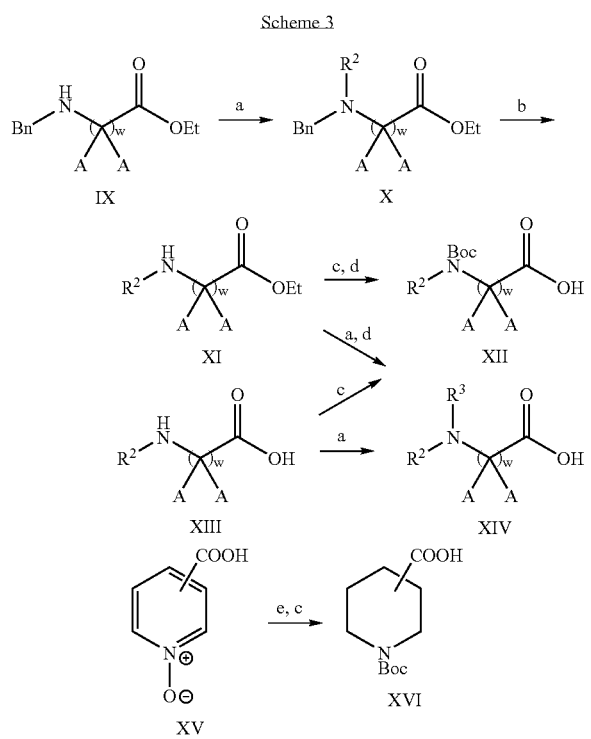

(a) Reductive amination or alkylation. (b) Deprotection. (c) Base/Boc₂O/DME.
(d) Hydrolysis. (e) HCOONH₄/10%Pd—C/MeOH.

The N-protected primary or secondary amino acids XII, tertiary amino acids XIV and N-protected piperidine carboxylic acids XVI, which are used as starting materials in Scheme 10, are either commercially available or prepared according to literature procedures as outlined in Scheme 3. For example, the N-protected amino acids XII and tertiary amino acids XIV are prepared from the corresponding ester XI, X, XI or carboxylic acid XIII. The N-protected piperidine carboxylic acids XVI may be prepared by reduction of the corresponding substituted pyridine or pyridine N-oxide XV, followed by Boc protection as shown in Scheme 3. (For representative reviews for the preparation of optically active α-amino acids, see: R. M. Williams, In *Synthesis of Optically Active α-Amino Acids*, J. E. Baldwin, Ed.; Organic Chemistry Series, Pergamon Press: Oxford, 1989; R. M. Williams, *Chem. Rev.* 1992, 92, 889; R. O. Duthaler, *Tetrahedron* 1994, 50, 1539; C. Cativiela, *Tetrahedron: Asymmetry* 1998, 9, 3517; C. Cativiela, *Tetrahedron: Asymmetry* 2000, 11, 645; M. J. O'Donnell, *Aldrichimica Acta* 2001, 3, 3-15; *Enzyme Catalysis in Organic Synthesis*; K. Drauz, H. Waldmann, Eds.; Wiley-VCH: Weinheim, 1995; *Stereoselective Biocatalysis*; R. N. Patel, Ed.; Marcel Dekker, New York, 2000; and K. Maruoka, *Chem. Rev.* 2003, 103, 3013-3028. For representative reviews on the preparation of optically active β-amino acids, see: *Enantioselective Synthesis of β-Amino Acids*; E. Juaristi, Wiley-VCH, New York, 1997; M. P. Sibi, *Tetrahedron* 2002, 58, 7991-8035; D. C. Cole, *Tetrahedron* 1994, 50, 9517-9582; E. Juaristi, *Aldrichim. Acta* 1994, 27, 3; G. Cardillo, *Chem. Soc. Rev.* 1996, 25, 117-128; Y. Yamamoto, N. Asgo and W. Tsukada, *Advances in Asymmetric Synthesis* (Ed.: A. Hassner), JAI Press, Stamford, 1998, p. 1. For the preparation of azepane carboxylic acids, see G. I. Georg et al., *Bioorg. Med. Chem. Lett.* 1991, 1, 125-128. For the preparation of piperidine carboxylic acids, see B. Zacharie et al., *J. Org. Chem.* 2001, 66, 5264-5265. For the preparation of pyrrolidine carboxylic acids, see R. Ling et al., *Tetrahedron* 2001, 57, 6579-6588; B. C. J. van Esseveldt et al., *SynLett* 2003, 15, 2354-2358. For the preparation of azetidine carboxylic acids, see S. Hanessian et al., *Bioorg. Med. Chem. Lett.* 1999, 9, 1437-1442; R. A. Miller et al., *Synth. Commun.* 2003, 33, 3347-3353 and references therein).

Scheme 4

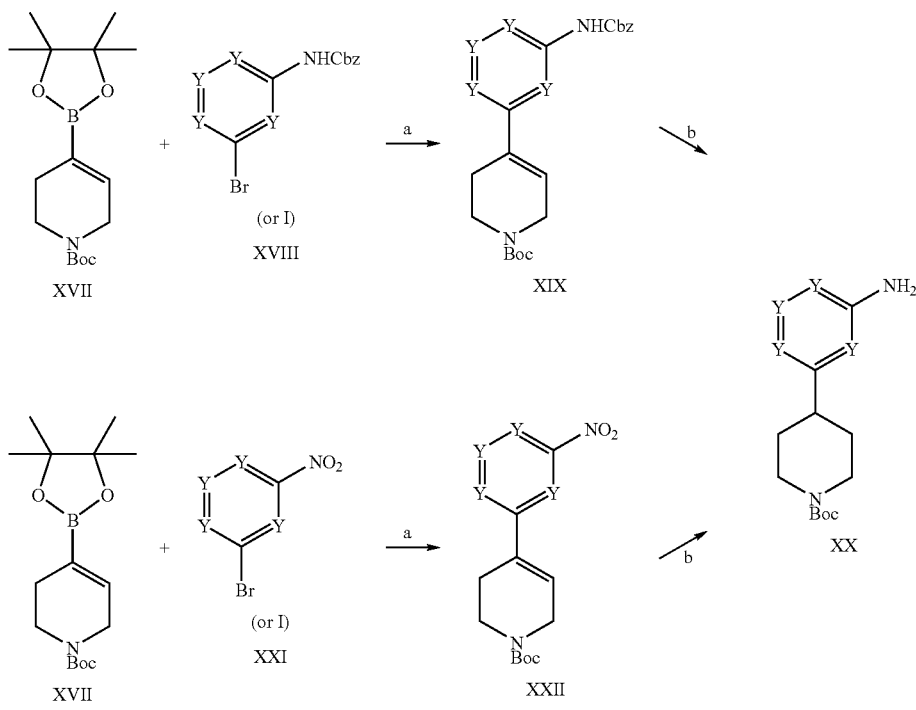

(a) K₂CO₃/PdCl₂dppf/DMF/60-80° C. overnight. (b) 10% Pd/C/H₂ (50-60 psi)/EtOH/rt 24-72 h.

Intermediate tert-butyl 4-(3-aminoaryl)piperidinecarboxylates of Formula XX are prepared as outlined in Scheme 4 from tert-butyl 4-(4,4,5,5-tetramethyl-1,3,2-dioxaborolan-2-yl)-1,2,5,6-tetrahydropyridine carboxylate XVII and N-Cbz protected bromo or iodo anilines or amino pyridines XVIII via Suzuki coupling followed by simultaneous reduction of the double bond in the tetrahydropyridine ring and removal of the Cbz protecting group by catalytic hydrogenation. Alternatively, tert-butyl 4-(3-aminoaryl)piperidinecarboxylate XX may be prepared from tert-butyl 4-(4,4,5,5-tetramethyl-1,3,2-dioxaborolan-2-yl)-1,2,5,6-tetrahydropyridine carboxylate XVII and bromo or iodo nitrobenzenes or nitropyridines XXI via Suzuki coupling followed by simultaneous reduction of the double bond and the nitro group by means of catalytic hydrogenation. (Suzuki coupling and hydrogenation reactions are described in the following references: A. Suzuki et al, *Chem. Rev.* 1995, 95, 2457; A. Suzuki, *J. Organomet. Chem.* 1999, 576, 147-168 and the references cited therein; and P. N. Rylander, *Hydrogenation Methods* (*Best Synthetic Methods Series*), Academic Press, 1990).

tert-Butyl 4-(4,4,5,5-tetramethyl-1,3,2-dioxaborolan-2-yl)-1,2,5,6-tetrahydropyridine carboxylate XVII which is used as starting material in Scheme 4 can be prepared according to the procedures described by P. R. Eastwood, *Tetrahedron Lett.* 2000, 41, 3705-3708 and references cited therein.

Scheme 5

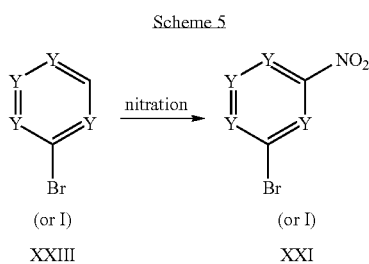

The 3-bromo or 3-iodo nitrobenzenes and nitropyridines XXI, which are used as starting materials for the synthesis outlined in Scheme 4, are available from commercial sources or may alternatively be prepared from the corresponding bromo or iodo benzenes and pyridines XXIII by nitration methods. General information regarding aromatic nitration is described in the following references: J. G. Hoggett, R. B. Moodie, J. R. Penton and K. Schofield, *Nitration and Aromatic Reactivity*, Cambridge University Press, London, 1971; K. Schofield, *Aromatic Nitration*, Cambridge University Press, London, 1980; and G. A. Olah, R. Malhotra and S. C. Narang, *Nitration: Methods and Mechanism*, (Ed.: H. Feuer), VCH Publishers, New York, 1989.

Scheme 6

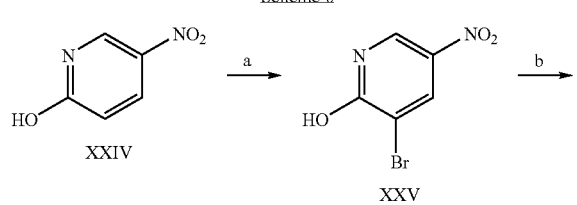

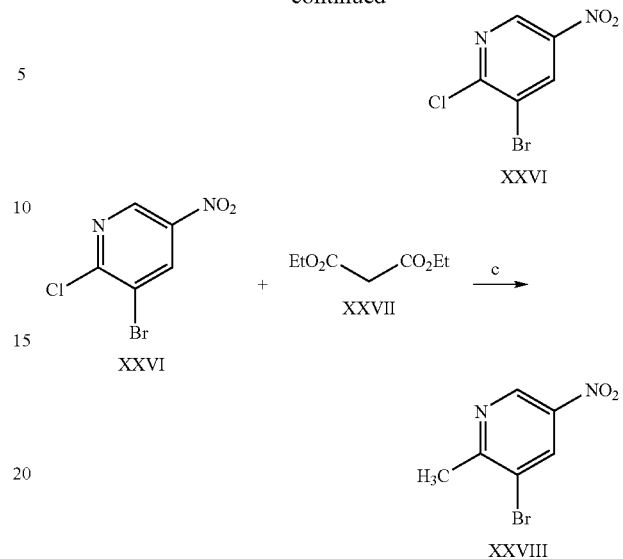

(a) Br$_2$. (b) POCl$_3$/quinoline. (c) NaH/Et$_2$O.

Alternatively, the substituted bromo or iodo nitrobenzenes or nitropyridines XXI may be prepared from commercially available materials via a series of functional group transformation methods known to those skilled in the art. For example, 3-bromo-2-methyl-5-nitropyridine XXVIII may be prepared and functionalized from 5-nitropyridin-2-ol XXIV as shown in Scheme 6.

Scheme 7

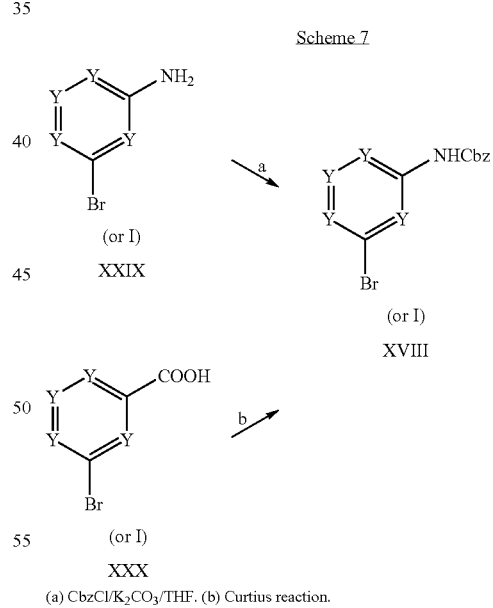

(a) CbzCl/K$_2$CO$_3$/THF. (b) Curtius reaction.

The N-Cbz bromo or iodo anilines and amino pyridines XVIII, which are used as starting materials in the syntheses outlined in Scheme 4, may be prepared by a variety of conditions from commercially available materials. For example, the amino group of commercially available bromo or iodo anilines and amino pyridines XXIX may be protected directly by benzyl chloroformate in the presence of base. Alternatively, N-Cbz protected bromo or iodo anilines and amino pyridines XVIII may be prepared from the corresponding benzoic acids, isonicotinic acids, nicotinic acids or picolinic acids XXX using diphenylphosphoryl azide via a Curtius type rearrangement, followed by trapping the isocyanates with benzyl alcohol as described by S. Yamada et al., *Tetrahedron* 1974, 30, 2151-2157.

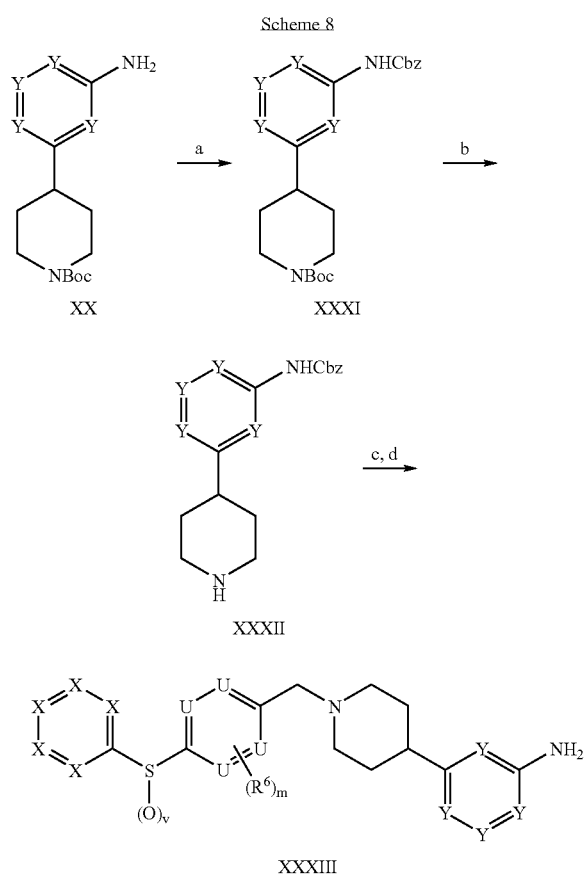

(a) CbzCl/K₂CO₃/THF. (b) 4 M HCl in 1,4-dioxane/rt 1 h or TFA/CH₂Cl₂/rt 10 min.
(c) aldehydes IV, V or VI/NaBH(OAc)₃/HOAc/CH₂Cl₂ or 1,2-dichloroethane or NaBH₃CN/MeOH. (d) KOH/MeOH/reflux, 10 h or BF₃/SMe₂/CH₂Cl₂/rt, 5 h.

The intermediates of Formula XXXIII are prepared as shown in Scheme 8. tert-Butyl 4-(3-aminoaryl)piperidinecarboxylate XX is acylated with CbzCl in the presence of base to afford tert-butyl 4-{3-[(phenylmethoxy)carbonylamino]aryl}piperidinecarboxylate XXXI. The Boc protecting group is removed under acidic conditions to give N-(3-(4-piperidyl)aryl)(phenylmethoxy)carboxamide XXXII. Reductive amination of piperidine XXXII with a variety of benzaldehydes of Formulas IV, V and VI using sodium triacetoxyborohydride or sodium cyanoborohydride followed by removal of the Cbz group under basic conditions or by treatment with BF₃/SMe₂ affords arylamines XXXIII.

Under similar conditions, the compounds of Formula XXXIII were also prepared via reductive amination with NaBH₃CN in MeOH from the corresponding aldehyde IV, V and VI and the piperidine moiety, wherein the anilinic nitrogen is unprotected.

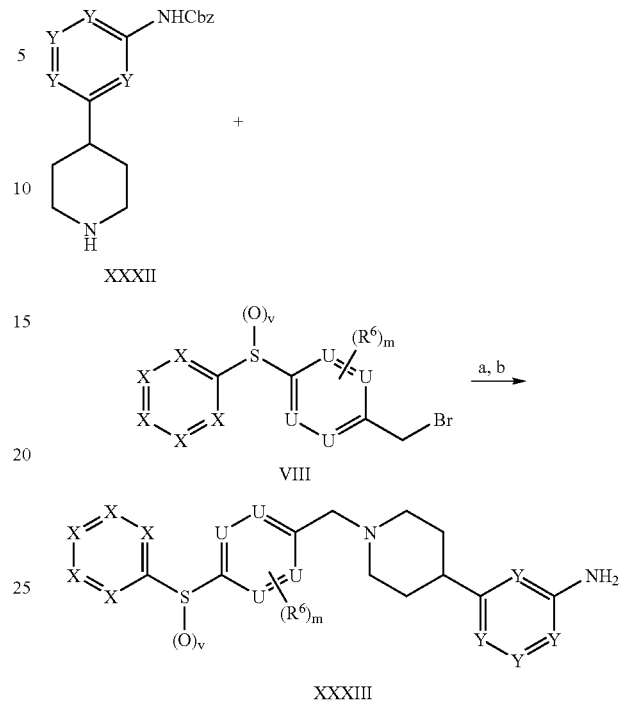

(a) K₂CO₃/DMF/90° C., 5 h.
(b) KOH/MeOH/reflux, 10 h or BF₃/SMe₂/CH₂Cl₂/rt, 5 h.

Alternatively, the arylamines XXXIII may be prepared via alkylation of piperidines XXXII with benzyl bromides VIII under basic conditions followed by hydrolysis or by treatment with BF₃/SMe₂ to remove the Cbz group.

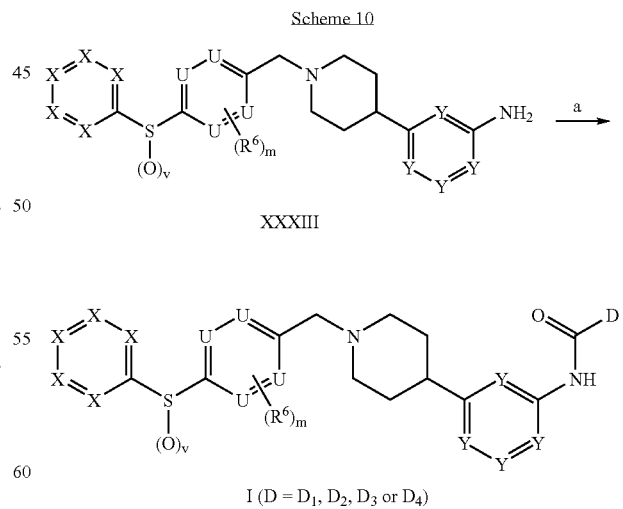

I (D = D₁, D₂, D₃ or D₄)

(a) acid chloride, chloroformate or carbamyl chloride/TEA/THF/rt.

Scheme 11

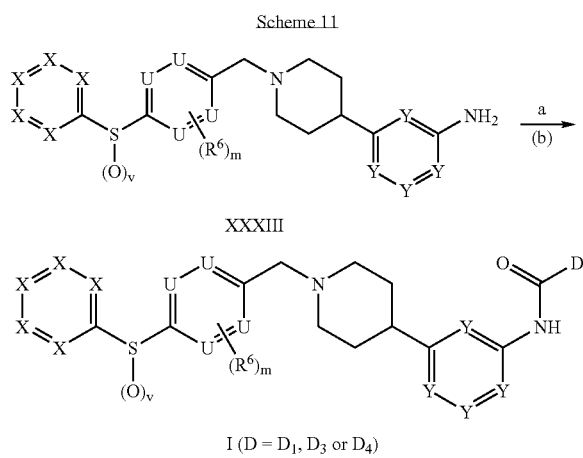

(a) amino acid/EDC/DMAP/CH$_2$Cl$_2$/rt. (b) deprotection (when R$^3$ = protecting group).

Compounds of the invention of Formula I (D=D$^1$, D$^2$, D$^3$ or D$^4$) are prepared as outlined in Scheme 10. 3-{1-[(4-arylthiophenyl)methyl]-4-piperidyl}arylamines XXXIII are acylated with acid chlorides, chloroformates or carbamyl chlorides under standard coupling conditions to give compounds of Formula I (D=D$^1$, D$^3$ or D$^4$) Compounds of the invention of Formula I (D=D$^1$, D$^2$, D$^3$ or D$^4$) are prepared as outlined in Scheme 11. 3-{1-[(4-arylthiophenyl)methyl]-4-piperidyl}arylamines XXXIII are acylated with N-protected amino acids (for primary and secondary amino acids) or amino acids (for tertiary amino acids) to provide the amide derivatives. For primary or secondary amino acids (R$^2$ or R$^3$=H) the protecting groups are removed using standard conditions. Compounds of the invention of Formula I (D=D$^2$, D$^5$, D$^6$, D$^7$, D$^8$ or D$^9$) are prepared as outlined in Scheme 12. The ureas and carbamates of Formula I (D=D$^2$, D$^5$, D$^6$, D$^7$, D$^8$ or D$^9$) are prepared by the reaction of an amine or an alcohol (N-protected if necessary) with 3-{1-[(4-arylthiophenyl)methyl]4-piperidyl}arylisocyanate XXXIV and N-[3-(1-{[4-arylthiophenyl]methyl}(4-piperidyl))aryl](4-nitrophenoxy)carboxamide XXXV, followed by removal of the protecting group (for R$^3$ or R$^2$=H) to give amines of Formula I (D=D$^2$, D$^5$, D$^6$, D$^7$, D$^8$ or D$^9$).

Scheme 12

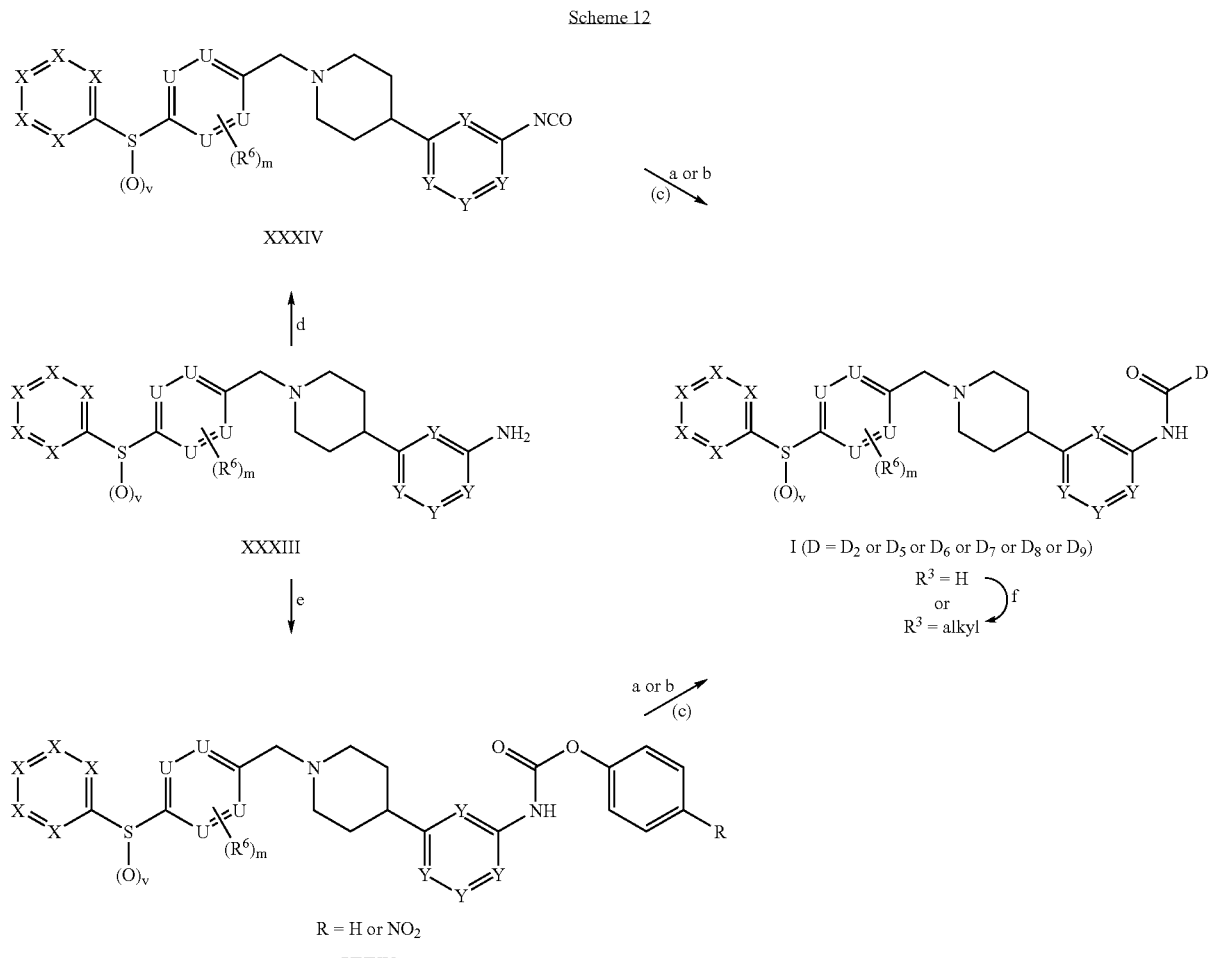

(a) amine or alcohol/base/CH$_2$Cl$_2$. (b) amine or alcohol/dioxane/heat or microwave.
(c) deprotection (when R$^3$ = protecting group). (d) Triphosgene/Et$_3$N/PhMe/70° C.
(e) Aryl chloroformate/pyridine/CH$_2$Cl$_2$. (f) reductive amination.

The 3-{1-[(4-arylthiophenyl)methyl]-4-piperidyl}arylisocyanates XXXIV are prepared from XXXIII by using triphosgene under standard conditions. The activated phenyl carbamates of Formula XXXV are prepared from XXXIII under standard conditions.

The primary and secondary amines with Formula I ($R^3$=H) may be further converted to tertiary amines ($R^3$=alkyl) via a reductive amination procedure. Any modification of the sequence in the schemes including the use of other protective groups or different conditions for amide, urea, carbamate formation would be apparent to those skilled in the art. The general information for protecting/deprotecting the amino group can be found in the textbook (T. Green and P. G. M. Wuts, *Protective Groups in Organic Synthesis*, John Wiley & Sons, Inc., New York, N.Y., 1999).

General Methods: All reactions were performed under a nitrogen atmosphere and the reagents, neat or in appropriate solvents, were transferred to the reaction vessel via syringe and cannula techniques. Anhydrous solvents were purchased from Aldrich Chemical Company and used as received. The NMR spectra were recorded at Bruker Avance (400 MHz) or GE QEPlus300 in $CDCl_3$, MeOH-$d_4$ or DMSO-$d_6$ as solvent with tetramethylsilane as the internal standard unless otherwise noted. Chemical shifts (δ) are expressed in ppm, coupling constants (J) are expressed in Hz, and splitting patterns are described as follows: s=singlet; d=doublet; t=triplet; q=quartet; quintet; sextet; septet; br=broad; m=multiplet; dd=doublet of doublets; dt=doublet of triplets; td=triplet of doublets; dm=doublet of multiplets; ddd=doublet of doublet of doublets. Elemental analyses were performed by Robertson Microlit Laboratories, Inc. Unless otherwise noted, mass spectra were obtained using electrospray ionization (ESMS, Micromass Platform II or Quattro Micro) and $(M+H)^+$ is reported. Thin-layer chromatography (TLC) was carried out on glass plates pre-coated with silica gel 60 $F_{254}$ (0.25 mm, EM Separations Tech.). Preparative TLC was carried out on glass sheets pre-coated with silica gel GF (2 mm, Analtech). Flash column chromatography was performed on Merck silica gel 60 (230-400 mesh). Melting points (mp) were determined in open capillary tubes on a Mel-Temp apparatus and are uncorrected. Microwave experiments were carried out using a Biotage Emyrs Optimizer™ or Smithcreator.

Preparation of Intermediates

Benzaldehyde Synthesis:

Intermediates of Formula IV 4-(4-chlorophenylthio)benzaldehyde:

A mixture of 4-fluorobenzaldehyde (12.6 mmol, 1.57 g), 4-chlorobenzenethiol (12.6 mmol, 1.81 g), $K_2CO_3$ (15.1 mmol, 2.09 g) in DMF (5.00 mL) was heated at 90° C. for 10 h. After cooling to room temperature, the reaction mixture was poured into a separatory funnel with water (100 mL). The phases were separated and the aqueous layer was extracted with $CH_2Cl_2$ (3×50 mL). The combined organic layers were washed with water (2×100 mL), brine (50 mL) and dried over $MgSO_4$. Removal of the solvents in vacuo gave a light yellow liquid. Purification by flash column chromatography (eluent: 5% EtOAc in Hexane) provided 4-(4-chlorophenylthio)benzaldehyde (2.00 g, 76.0% yield) as a light yellow liquid. $^1$H NMR ($CDCl_3$) δ 9.93 (s, 1H), 7.72 (d, J=8.3 Hz, 2H), 7.46-7.39 (m, 4H), 7.25 (d, J=8.3 Hz, 2H).

The following intermediates of Formula IV were prepared analogously:

6-(Pyridin-2-ylsulfanyl)-pyridine-3-carbaldehyde:

To a solution of 2-mercaptopyridine (6.39 g, 57.4 mmol) in DMF (100 mL) was added NaH (60% dispersion in oil, 2.29 g, 57.2 mmol) in portions and the mixture was stirred for 15 min. 6-Bromo-3-pyridine carboxaldehyde (9.28 g, 49.9 mmol) was added and the resultant mixture was stirred for 1 h. Water was added followed by the addition of EtOAc. The phases were separated and the aqueous layer was extracted with EtOAc (2×). The organic extracts were combined, dried over $Na_2SO_4$, filtered and concentrated in vacuo to give a crude product which was purified by flash column chromatography (eluents: 20% EtOAc in hexanes and 30% EtOAc in hexanes). Evaporation of the appropriate fractions gave a white solid, which was further purified by recrystallization from diethyl ether to give the product as a white solid (9.66 g, 90% yield). $^1$H NMR ($CDCl_3$) δ 10.00 (s, 1H), 8.89-8.84 (m, 1H), 8.67-8.64 (m, 1H), 8.01 (dd, J=2.2, 8.9 Hz, 1H), 7.76 (dt, J=2.2, 8.3 Hz, 1H), 7.67-7.63 (m, 1H), 7.44 (d, J=8.3 Hz, 1H), 7.35-7.29 (m, 1H).

6-(Pyridin-4-ylsulfanyl)-pyridine-3-carbaldehyde:

To a solution of 4-mercaptopyridine (5.59 g, 50.3 mmol) in DMF (100 mL) was added NaH (60% dispersion in oil, 1.99 g, 49.7 mmol) in portions and the mixture was stirred for 20 min. 6-Bromo-3-pyridine carboxaldehyde (9.22 g, 49.6 mmol) was added and the resultant mixture was stirred for 1 h. Water was added followed by the addition of EtOAc. The phases were separated and the aqueous layer was extracted with EtOAc (2×). The organic extracts were combined, dried over $Na_2SO_4$, filtered and concentrated in vacuo to give a crude product, which was purified by recrystallization from EtOAc. The resultant colored solid was filtered through a silica gel column (eluent: MTBE). Evaporation of the filtrate and further recrystallization from MTBE gave the product as a white solid (8.1 g, 76% yield).

$^1$H NMR ($CDCl_3$) δ 10.03 (s, 1H), 8.89-8.86 (m, 1H), 8.68-8.64 (m, 2H), 8.04 (dd, J=2.2, 8.9 Hz, 1H), 7.52-7.48 (m, 2H), 7.33-7.28 (m, 1H).

4-(5-Trifluoromethyl-pyridin-2-ylsulfanyl)-benzaldehyde: A mixture of 5-trifluoromethyl-pyridine-2-thiol (6.99 g, 39.0 mmol), 4-fluorobenzaldehyde (4.79 g, 38.6 mmol), anhydrous $K_2CO_3$ (8.16 g, 59.1 mmol) and DMF (70 mL) was heated at 110° C. for 18 h. The mixture was cooled to room temperature and partitioned between MTBE and water. The phases were separated. The organic extracts were combined, dried over $Na_2SO_4$, filtered and evaporated to give a crude product which was purified by flash column chromatography (eluent: 5% MTBE in petroleum ether). Evaporation of the appropriate fractions gave the product (9.47 g, 87% yield). $^1$H NMR ($CDCl_3$) δ 10.06 (s, 1H), 8.69-8.66 (m, 1H), 7.97-7.92 (m, 2H), 7.78-7.72 (m, 3H), 7.23-7.16 (m, 1H).

Intermediate of Formula V

4-[(4-chlorophenyl)sulfinyl]benzaldehyde:

A mixture of 4-(4-chlorophenylthio)benzaldehyde (3.63 mmol, 900 mg), 3-chloroperoxybenzoic acid (max 77%, 3.63 mmol, 813 mg) and $CH_2Cl_2$ (5.00 mL), was stirred at room temperature for 60 min and poured into a separatory funnel with 5% aqueous KOH solution (10 mL). The phases were separated and the aqueous layer was extracted with $CH_2Cl_2$ (3×10 mL) and the combined organic extracts were washed with water (10 mL), brine (50 mL) and dried over $MgSO_4$. Removal of solvents in vacuo gave a light yellow liquid. Purification by flash column chromatography (eluent: 5% EtOAc in Hexane) provided 4-[(4-chlorophenyl)sulfinyl]benzaldehyde (500 mg, 52.2% yield) as a light yellow solid. ¹H NMR (CDCl₃) δ 10.04 (s, 1H), 7.98 (d, J=8.2 Hz, 2H), 7.82 (d, J=8.2 Hz, 2H), 7.62 (d, J=8.5 Hz, 2H), 7.46 (d, J=8.5 Hz, 2H).

Intermediate of Formula VI

4-[(4-chlorophenyl)sulfonyl]benzaldehyde:

A mixture of 4-(4-chlorophenylthio)benzaldehyde (3.63 mmol, 900 mg), 3-chloroperoxybenzoic acid (max 77%, 10.9 mmol, 2.44 g) in CH₂Cl₂ (5.00 mL) was stirred at room temperature for 60 min and poured into a separatory funnel with 5% aqueous KOH solution (20 mL). The phases were separated and the aqueous layer was extracted with CH₂Cl₂ (3×10 mL). The combined organic layers were washed with water (10 mL), brine (50 mL) and dried over MgSO₄. Removal of solvents in vacuo gave a light yellow liquid. Purification by flash column chromatography (eluent: 5% EtOAc in Hexane) provided 4-[(4-chlorophenyl)sulfonyl]benzaldehyde (700 mg, 68.9% yield) as a light yellow solid.

¹H NMR (CDCl₃) δ 10.09 (s, 1H) 8.11-8.00 (m, 4H), 7.91 (d, J=8.7 Hz, 2H), 7.51 (d, J=8.7 Hz, 2H).

Benzyl Bromide Synthesis

Intermediate of Formula VIII 4-(bromomethyl)-1-[(4-methylphenyl)sulfinyl]benzene:

A mixture of 4-methyl-1-[(4-methylphenyl)sulfinyl]benzene (1.15 g, 5.00 mmol), N-bromosuccinimide (1.08 g, 6.00 mmol), 2,2'-azobis-(2-methylpropionitrile) (100 mg, 0.600 mmol), and CCl₄ (25.0 mL) as solvent was stirred for 5 min at room temperature and then heated to reflux for 12 h. The reaction mixture was cooled to room temperature and filtered and the solvent was removed in vacuo, affording a crude product which was used in the next step without any further purification (1.21 g, 78.1% yield). ¹H NMR (CDCl₃) δ 7.71-7.57 (m, 2H), 7.57-7.40 (m, 4H), 7.36-7.16 (m, 2H), 4.46 (s, 2H), 2.37 (s, 3H).

tert-butyl 4-(3-aminoaryl)piperidinecarboxylate synthesis:

Intermediate of Formula XVII tert-butyl 4-(4,4,5,5-tetramethyl-1,3,2-dioxaborolan-2-yl)-1,2,5,6-tetrahydropyridine carboxylate was prepared according to the procedures described by P. R. Eastwood, *Tetrahedron Lett*. 2000, 41, 19, 3705-3708 and references cited therein.

Intermediates of Formula XVII

1-Bromo-2,4-difluoro-5-nitrobenzene: To a 0° C. mixture of 1-bromo-2,4-difluorobenzene (20.0 g, 11.7 mL, 0.100 mol) and H₂SO₄ (76.8 mL) was added HNO₃ (68.0 mL) over 45 min at such a rate that the internal temperature was <7° C. The resulting mixture was stirred for 1 h at 0° C., poured into ice water (400 mL), stirred vigorously for 2-3 min and extracted with CH₂Cl₂ (400 mL). The organic layers were washed with brine (1×500 mL), dried over Na₂SO₄, filtered and evaporated to give the product as a yellow oil (23.5 g, 95% yield). ¹H NMR (CDCl₃) δ 8.39 (t, J=7.2 Hz, 1H), 7.14 (ddd, J=0.3, 7.8, 9.9 Hz, 1H).

2-Bromo-5-fluoro-4-nitro toluene: To a mixture of nitronium tetrafluoroborate (11.6 g; 87.0 mmol) and CH₂Cl₂ (60.0 mL) was added 2-bromo-5-fluoro toluene (15.0 g, 10.0 mL, 79.0 mmol) over 5 min. After refluxing for 4.5 h, the mixture was cooled to room temperature and poured into ice water (150 mL). The mixture was extracted with CH₂Cl₂ (3×50 mL). The combined organic layers were washed with brine (100 mL), dried over Na₂SO₄, filtered and concentrated to give 18.3 g of crude product. The crude product was treated with hexane and cooled to −70° C. then the hexane was decanted away from the resulting solid to give the desired product as a semi-solid (9.77 g, 53% yield). The mother liquors were concentrated in vacuo and purified by flash column chromatography (eluent: 2% EtOAc in Hexane) to give the desired product (1.0 g). ¹H NMR (CDCl₃) δ 8.26 (d, J=6.9 Hz, 1H), 7.20 (d, J=11.7 Hz, 1H), 2.48 (s, 3H).

1-Bromo-3-nitro-2,4,6-trifluorobenzene: To a cooled (1.3° C.) mixture of 1-bromo-2,4,6-trifluorobenzene (30.0 g, 142 mmol) and H₂SO₄ (115 mL) was added HNO₃ (68%, 102 mL) over 1.5 h at such a rate that the internal temperature was <8° C. After stirring at 0° C. for 2 h, the resulting mixture was poured into ice water (1850 mL), stirred vigorously for 30 min and extracted with CH₂Cl₂ (3×600 mL). The combined organic layers were washed with water (2×600 mL), dried over MgSO₄, filtered and concentrated in vacuo to give the desired product as a clear yellow oil (35.0 g, 99% yield). ¹H NMR (CDCl₃) δ 7.01 (ddd, J=2.4, 7.8, 9.3 Hz, 1H); ¹⁹F NMR (CDCl₃) δ −116.20 to −116.10, −107.73 to −107.71, −93.80 to −93.70.

3-Bromo-2-methyl-5-nitropyridine:

Intermediate of Formula XXV

Step 1: A mixture of 2-hydroxy-5-nitropyridine (50.0 g, 0.358 mol) and water (7 L) was warmed to 40° C. and bromine (21.1 mL, 0.393 mol) was added dropwise over ~20 min. After stirring at 40° C. for 2.5 h, the mixture was cooled to 10° C. and the crude product was isolated by filtration. The solid was washed with water and dried in vacuo to give 3-bromo-2-hydroxy-5-nitropyridine as a solid (70.0 g, 90% yield). mp 212-214° C. (with decomposition); ¹H NMR (CD₃OD) δ 8.66 (d, J=2.9 Hz, 1H), 8.64 (d, J=2.9 Hz, 1H).

Intermediate of Formula XXVI

Step 2: To a cooled (0-5° C.) mixture of 3-bromo-2-hydroxy-5-nitropyridine (47.0 g, 0.214 mol) and quinoline (13.7 g, 0.107 mol) was added POCl₃ (26.0 mL, 0.278 mol) dropwise over ~10 min (the mixture was difficult to stir initially but became less viscous as the reaction progressed and the mixture warmed). After stirring at 120° C. for 3.5 h, the mixture was cooled to 100° C. and water (90 mL) was added. The resulting mixture was stirred vigorously while cooling to 0-5° C. The product was collected by filtration, washed with water and dried in vacuo at 45° C. to give 3-bromo-2-chloro-5-nitropyridine (42.0 g, 82% yield). ¹H NMR (CD₃OD) δ 9.19 (d, J=2.4 Hz, 1H), 8.93 (d, J=2.4 Hz, 1H).

Intermediate of Formula XXVIII

Step 3: To a cooled (15° C.) solution of diethyl malonate (8.8 mL, 58.0 mmol) in diethyl ether (110 mL) was added NaH (60% dispersion in oil, 2.32 g, 58.0 mmol) over 5 min and 3-bromo-2-chloro-5-nitropyridine (12.5 g, 52.6 mmol) in four portions over ~15 min (an exotherm to 26° C. was observed), followed by removal of diethyl ether in vacuo to give a red oil. After stirring the resulting red oil at 114° C. for 1 h 15 min, H₂SO₄ (6M, 67.0 mL) was added. The resulting mixture was heated at reflux for 8 h then cooled to 0° C. and the pH value was adjusted to 7 with 25% KOH aqueous solution (135 mL). The resulting mixture was stirred in an ice bath for 25 min and the crude product was collected and washed with water (50 mL) by filtration. The crude product was stirred in CH₂Cl₂ (350 mL) for 30 min and the impurity was removed by filtration. The organic layer was dried over Na₂SO₄, filtered and concentrated to give the impure product as red oil (11.1 g). The red oil was dissolved in CH₂Cl₂ (100 mL) and hexanes (200 mL). The resulting mixture was filtered and the organic portion was concentrated in vacuo to give 3-bromo-2-methyl-5-nitropyridine as an orange crystalline solid (9.30 g, 81% yield). $^1$H NMR (CDCl$_3$) δ 9.25 (d, J=2.3 Hz, 1H), 8.61 (d, J=2.3 Hz, 1H), 2.80 (s, 3H).

Intermediate of Formula XVIII

Benzyl 5-bromo-3-pyridinyl carbamate: To a suspension of 5-bromonicotinic acid (20.0 g, 99.0 mmol) in toluene (200 mL) was added diphenylphosphoryl azide (25.6 mL, 118.8 mmol) and Et$_3$N (16.6 mL, 118.8 mmol). After stirring at room temperature for 30 min, benzyl alcohol (15.4 mL, 148.5 mmol) was added. The mixture was stirred at room temperature for 1 h then refluxed overnight. After cooling to room temperature, the reaction mixture was washed with H$_2$O, saturated aqueous NaHCO$_3$ and brine, dried over MgSO$_4$ and concentrated. Purification by flash column chromatography (eluent: 15-50% EtOAc in Hexane) provided benzyl 5-bromo-3-pyridinylcarbamate (22.2 g, 72.5 mmol, 73% yield): $^1$H NMR (CDCl$_3$) δ 8.39-8.32 (m, 2H), 8.29 (s, 1H), 7.45-7.32 (m, 5H), 6.94 (s, 1H), 5.22 (s, 2H); ESMS m/e: 307.0 (M+H)$^+$.

Intermediates of Formula XX tert-Butyl 4-(3-aminophenyl)piperidine carboxylate, tert-butyl 4-(3-amino-4-fluorophenyl) piperidine carboxylate, tert-butyl 4-(3-amino-4,6-difluorophenyl)piperidine carboxylate were prepared according to the procedures described by M. R. Marzabadi et al. in PCT WO 2004/005257 A1 (pp. 48-82).

The following intermediates were prepared analogously:

tert-Butyl 4-(3-amino-6-methylphenyl)piperidinecarboxylate:

$^1$H NMR (CDCl$_3$) δ 6.93 (d, J=8.1 Hz, 1H), 6.53 (d, J=2.4 Hz, 1H), 6.47 (dd, J=2.4, 8.1 Hz, 1H), 4.30-4.18 (m, 2H), 3.53 (brs, 2H), 2.86-2.51 (m, 3H), 2.23 (s, 3H), 1.77-1.68 (m, 2H), 1.50-1.63 (m, 2H), 1.49 (s, 9H).

tert-Butyl 4-(3-amino-6-fluorophenyl)piperidinecarboxylate:

$^1$H NMR (CDCl$_3$) δ 6.85-6.76 (m, 1H), 6.51-6.44 (m, 2H), 4.30-4.15 (m, 2H), 3.51 (brs, 2H), 2.98-2.73 (m, 3H), 1.82-1.73 (m, 2H), 1.66-1.50 (m, 2H), 1.48 (s, 9H).

tert-Butyl 4-(3-amino-4-fluoro-6-methylphenyl)piperidinecarboxylate:

$^1$H NMR (CDCl$_3$) δ 6.77 (d, J=12.0 Hz, 1H), 6.60 (d, J=9.0 Hz, 1H), 4.32-4.16 (m, 2H), 3.86-3.52 (br, 2H), 2.86-2.67 (m, 3H), 2.22 (s, 3H), 1.69 (m, 2H), 1.60-1.43 (m, 11H).

tert-Butyl 4-(3-amino-2,4,6-trifluorophenyl)piperidinecarboxylate:

$^1$H NMR (CDCl$_3$) δ 6.67-6.54 (m, 1H), 4.32-4.15 (m, 2H), 3.60-3.48 (m, 2H), 3.10-2.97 (m, 1H), 2.84-2.68 (m, 2H), 2.06-1.88 (m, 2H), 1.70-1.60 (m, 2H), 1.46 (s, 9H).

tert-Butyl 4-(5-amino-3-pyridyl) piperidinecarboxylate:

$^1$H NMR (CDCl$_3$) δ 8.01-7.95 (m, 1H), 7.89 (s, 1H), 6.83 (s, 1H), 4.39-4.09 (br, 2H), 3.90-3.50 (br, 2H), 2.88-2.68 (m, 2H), 2.67-2.52 (m, 1H), 1.88-1.71 (m, 2H), 1.68-1.49 (m, 2H), 1.48 (s, 9H); ESMS m/e: 278.3 (M+H)$^+$.

tert-Butyl 4-(5-amino-2-methyl-3-pyridyl)piperidinecarboxylate:

$^1$H NMR (CDCl$_3$) δ 7.87 (d, J=2.7 Hz, 1H), 6.80 (d, J=2.7 Hz, 1H), 4.33-4.17 (m, 2H), 3.57-3.50 (br, 2H), 2.88-2.70 (m, 3H), 2.46 (s, 3H), 1.79-1.70 (m, 2H), 1.61-1.43 (m, 11H).

3-{1-[(4-arylthiophenyl)methyl]-4-piperidyl}phenylamine synthesis:

3-(1-{[4-(4-methoxyphenylthio)phenyl]methyl}(4-piperidyl))-4-methylphenylamine:

Intermediate of Formula XXXI

Step 1: Benzyl chloroformate (95%, 4.52 mL, 30.1 mmol) was added dropwise to a stirred mixture of tert-butyl 4-(3-amino-6-methylphenyl)piperidinecarboxylate (6.99 g, 24.1 mmol) and K$_2$CO$_3$ (3.66 g, 26.4 mmol) in tetrahydrofuran (350 mL) and stirred under nitrogen for 18 h. CH$_2$Cl$_2$ was added to the reaction mixture, washed with NaHCO$_3$ solution (saturated), followed by water, then dried over Na$_2$SO$_4$ and concentrated in vacuo to give an oil. Purification by flash column chromatography (eluent: cyclohexane:EtOAc (87:13)) gave tert-butyl 4-{2-methyl-5-[(phenylmethoxy)carbonylamino]phenyl}piperidinecarboxylate (7.90 g, 77.1% yield) as a white foam. ESMS m/e: 425.0 (M+H)$^+$.

Intermediate of Formula XXXII

Step 2: tert-Butyl 4-{2-methyl-5-[(phenylmethoxy)carbonylamino]phenyl}piperidine carboxylate (7.50 g, 17.6 mmol) was dissolved in CH$_2$Cl$_2$ (120 mL) and a HCl solution (4M in dioxane, 52.0 mL) was added and stirred for 1 h. The mixture was concentrated in vacuo and redissolved in CH$_2$Cl$_2$. Aqueous Na$_2$CO$_3$ solution (1 M) was added and the biphasic mixture was stirred for 20 min and separated. The organic layer was further washed with water, dried over Na$_2$SO$_4$ and concentrated in vacuo to afford N-(4-methyl-3-(4-piperidyl)phenyl)(phenylmethoxy)carboxamide (5.61 g, 98% yield) as a white solid. ESMS m/e: 326.0 (M+H)$^+$.

Intermediate of Formula XXXIII

Step 3: A mixture of N-(4-methyl-3-(4-piperidyl)phenyl)(phenylmethoxy)carboxamide (324 mg, 1.00 mmol) and 4-(4-methoxyphenylthio)benzaldehyde (244 mg, 1.00 mmol), dichloroethane (5.00 mL), acetic acid (60.0 mg, 1.00 mmol) and sodium triacetoxborohydride (424 mg, 2.00 mmol) was stirred under nitrogen at room temperature for 18 h. Saturated NaHCO$_3$ solution and CH$_2$Cl$_2$ was added. The mixture was separated, and the organic layer was washed with water (10 mL), dried over Na$_2$SO$_4$ and concentrated in vacuo. Purification by flash column chromatography (eluent: cyclohexane:EtOAc (85:15 then 7:3)) gave N-[3-(1-{[4-(4-methoxyphenylthio)phenyl]methyl}(4-piperidyl))-4-methylphenyl](phenylmethoxy) carboxamide (486 mg, 88.0% yield) as a white foam. ESMS m/e: 553.2 (M+H)$^+$.

Under similar conditions, the compounds of Formula XXXIII were also prepared via reductive aminination with NaBH$_3$CN in MeOH from the corresponding aldehyde IV, V and VI and the piperidine moiety, wherein the anilinic nitrogen is unprotected.

Step 4: N-[3-(1-{[4-(4-methoxyphenylthio)phenyl]methyl}(4-piperidyl))-4-methylphenyl] (phenylmethoxy)carboxamide (486 mg, 0.881 mmol) was dissolved in methanol (10.0 mL) and a KOH solution (40%, 1.20 mL) was added. The reaction mixture was heated at 100° C. for 10 h. After cooling to room temperature, the reaction mixture was poured into a separatory funnel. The phases were separated and the aqueous phase was extracted with CH$_2$Cl$_2$ (2×20 mL). The combined organic layers were washed with brine, dried over Na$_2$SO$_4$, filtered and concentrated in vacuo. Purification by flash column chromatography (eluent: Hexane:EtOAc (1:1 then 1:4)) gave 3-(1-{[4-(4-methoxyphenylthio)phenyl]methyl}(4-piperidyl))-4-methylphenylamine (362 mg, 98.2% yield). $^1$H NMR (400 MHz; CDCl$_3$) δ 7.43-7.35 (m, 4H), 7.24-7.11 (m, 3H), 6.93-6.85 (m, 2H), 6.63-6.58 (m, 1H), 6.48-6.42 (m, 1H), 3.82 (s, 3H), 3.48 (s, 2H), 3.03-2.91 (m, 2H), 2.68-2.54 (m, 1H), 2.20 (s, 3H), 2.13-1.98 (m, 2H), 1.79-1.64 (m, 4H). ESMS m/e: 419.2 (M+H)$^+$.

The following intermediates of Formula XXXIII were prepared analogously:

1-[(4-{[4-(3-amino-6-methylphenyl)piperidyl]methyl}phenyl)sulfonyl]4-chlorobenzene: ESMS m/e: 455.2 (M+H)$^+$.

3-(1-{[4-(3,4-difluorophenylthio)phenyl]methyl}(4-piperidyl))$_4$-methylphenylamine: ESMS m/e: 425.2 (M+H)$^+$.

4-methyl-3-{1-[(4-(2-pyridylthio)phenyl)methyl](4-piperidyl)}phenylamine: ESMS m/e: 390.2 (M+H)$^+$.

4-methyl-3-(1-{[4-(4-methylphenylthio)phenyl]methyl}(4-piperidyl))phenylamine: ESMS m/e: 403.2 (M+H)$^+$.

4-{[4-(3-amino-6-methylphenyl)piperidyl]methyl}-1-[(4-methylphenyl)sulfonyl]benzene: ESMS m/e: 435.1 (M+H)$^+$.

4-[(4-{[4-(3-amino-6-methylphenyl)piperidyl]methyl}phenyl)sulfonyl]-1,2-difluorobenzene: ESMS m/e: 457.2 (M+H)$^+$.

4-{[4-(3-amino-6-methylphenyl)piperidyl]methyl}-1-(phenylsulfonyl)benzene: ESMS m/e: 421.2 (M+H)$^+$.

4-methyl-3-{1-[(4-phenylthiophenyl)methyl](4-piperidyl)}phenylamine: ESMS m/e: 389.2 (M+H)$^+$.

The following intermediates of Formula XXXIII were prepared by direct reductive amination with NaBH$_3$CN in MeOH according to the procedure set forth in Step 3:

3-(1-{[4-(4-chlorophenylthio)phenyl]methyl}(4-piperidyl))-4-methylphenylamine: ESMS m/e: 423.2 (M+H)$^+$.

1-[(4-{[4-(3-amino-6-methylphenyl)piperidyl]methyl}phenyl)sulfinyl]-4-chlorobenzene: ESMS m/e: 439.2 (M+H)$^+$.

4-[(4-{[4-(3-amino-6-methylphenyl)piperidyl]methyl}phenyl)sulfinyl]-1,2-difluorobenzene: ESMS m/e: 441.1 (M+H)$^+$.

3-[(4-{[4-(3-amino-6-methylphenyl)piperidyl]methyl}phenyl)sulfonyl]-1-fluorobenzene: ESMS m/e: 439.2 (M+H)$^+$.

4-{[4-(3-amino-6-methylphenyl)piperidyl]methyl}-1-[(3,5-dimethylphenyl) sulfonyl]benzene: ESMS m/e: 449.2 (M+H)$^+$.

3-(1-{[4-(3-chlorophenylthio)phenyl]methyl}(4-piperidyl))-4-methylphenylamine: ESMS m/e: 423.2 (M+H)$^+$.

3-[(4-{[4-(3-amino-6-methylphenyl)piperidyl]methyl}phenyl)sulfinyl]-1-chlorobenzene: ESMS m/e: 439.1 (M+H)$^+$.

4-[(4-{[4-(3-amino-6-methylphenyl)piperidyl]methyl}phenyl)sulfonyl]-2-chloro-1-fluorobenzene: ESMS m/e: 473.1 (M+H)$^+$.

4-[(4-{[4-(3-amino-6-methylphenyl)piperidyl]methyl}phenyl)sulfinyl]-2-chloro-1-fluorobenzene: ESMS m/e: 457.1 (M+H)$^+$.

EXAMPLES

Example 1a

N-[3-(1-{[4-(4-fluorophenylthio)phenyl]methyl}(4-piperidyl))-4-methylphenyl]2-methylpropanamide:

2-methyl-N-(4-methyl-3-(4-piperidyl)phenyl)propanamide (130 mg, 0.500 mmol) and 4-(4-fluorophenylthio)benzaldehyde (116 mg, 0.500 mmol) were dissolved in dichloroethane (5.00 mL) and acetic acid (30.0 mg, 0.500 mmol), and sodium triacetoxyborohydride (212 mg, 1.00 mmol) was added at room temperature. Stirring was continued under nitrogen at room temperature for 10 h, then a saturated aqueous NaHCO$_3$ solution and CH$_2$Cl$_2$ was added. The phases were separated, and the organic phase was washed with water, dried over Na$_2$SO$_4$ and concentrated in vacuo. Purification by flash column chromatography (eluent: cyclohexane:EtOAc (85:15 then 7:3)) gave N-[3-(1-{[4-(4-fluorophenylthio)phenyl]methyl}(4-piperidyl))-4-methylphenyl]-2-methylpropanamide (86.3 mg, 36.2% yield) as a white solid. $^1$H NMR (CDCl$_3$) δ 7.43-7.32 (m, 3H), 7.31-7.22 (m, 5H), 7.09-6.98 (m, 4H), 3.51 (s, 2H), 3.04-2.93 (m, 2H), 2.76-2.61 (m, 1H), 2.52-2.41 (m, 1H), 2.27 (s, 3H), 2.14-2.03 (m, 2H), 1.86-1.65 (m, 4H), 1.25 (d, 6H, J=7.026 Hz); ESMS m/e: 477.2 (M+H)$^+$.

The following intermediates were prepared analogously:

Example 1b

N-[4-fluoro-3-(1-{[4-(4-fluorophenylthio)phenyl]methyl}(4-piperidyl))phenyl](methylethoxy)carboxamide ESMS m/e: 497.2 (M+H)$^+$.

Example 1c

Cyclopropyl-N-[2-fluoro-5-(1-{[4-(4-fluorophenylthio)phenyl]methyl}(4-piperidyl))-4-methylphenyl]carboxamide ESMS m/e: 493.3 (M+H)$^+$.

Example 1d

N-[3-(1-{[4-(4-chlorophenylthio)phenyl]methyl}(4-piperidyl))-4-methylphenyl]2-methylpropanamide ESMS m/e: 493.2 (M+H)$^+$.

Example 1e

N-[5-(1-{[4-(4-chlorophenylthio)phenyl]methyl}(4-piperidyl))-2-fluoro-4-methyl phenyl]-2-methylpropanamide ESMS m/e: 511.1 (M+H)$^+$.

Example 1f

N-[3-(1-{[4-(4-chlorophenylthio)phenyl]methyl}(4-piperidyl))-4-methylphenyl]methoxycarboxamide ESMS m/e: 481.1 (M+H)$^+$.

Example 1g

N-[5-(1-{[4-(4-chlorophenylthio)phenyl]methyl}(4-piperidyl))-6-methyl(3-pyridyl)]cyclobutylcarboxamide ESMS m/e: 506.2 (M+H)$^+$.

Example 1h

N-[5-(1-{[4-(4-chlorophenylthio)phenyl]methyl}(4-piperidyl))-6-methyl(3-pyridyl)]methoxycarboxamide ESMS m/e: 482.1 (M+H)$^+$.

Example 1i (dimethylamino)-N-[3-(1-{[4-(4-chlorophenylthio)phenyl]methyl}(4-piperidyl))-4-methylphenyl]carboxamide ESMS m/e: 494.2 (M+H)$^+$.

Example 1j

N-[3-(1-{[4-(4-chlorophenylthio)phenyl]methyl}(4-piperidyl))-2,4,6-trifluoro phenyl]-2-methylpropanamide ESMS m/e: 533.2 (M+H)$^+$.

Example 1k 2-(dimethylamino)-N-[3-(1-{[4-(4-chlorophenylthio)phenyl]methyl}(4-piperidyl))-4-methylphenyl]acetamide ESMS m/e: 508.2 (M+H)$^+$.

Example 1l

N-[3-(1-{[4-(3-fluorophenylthio)phenyl]methyl}(4-piperidyl))-4-methylphenyl]2-methylpropanamide ESMS m/e: 477.2 (M+H)$^+$.

Example 1m

N-[3-(1-{[4-(2,4-difluorophenylthio)phenyl]methyl}(4-piperidyl))-4-methyl phenyl]-2-methylpropanamide ESMS m/e: 495.3 (M+H)$^+$; Anal. Calcd. for $C_{29}H_{32}F_2N_2OS+HCl+0.17CH_2Cl_2$: C, 64.22; H, 6.16; N, 5.13. Found: C, 64.93; H, 6.15; N, 4.80.

Example 1n

N-[3-(1-{[4-(3-chloro-4-fluorophenylthio)phenyl]methyl}(4-piperidyl))-4-methyl phenyl]-2-methylpropanamide ESMS m/e: 511.2 (M+H)$^+$.

Example 1o

N-[3-(1-{[4-(2-fluorophenylthio)phenyl]methyl}(4-piperidyl))-4-methylphenyl]2-methylpropanamide ESMS m/e: 477.2 (M+H)$^+$.

Example 1p 2-methyl-N-(4-methyl-3-{1-[(4-(2-pyridylthio)phenyl)methyl](4-piperidyl)}phenyl)propanamide ESMS m/e: 460.3 (M+H)$^+$; Anal Calcd for $C_{28}H_{33}N_3OS+HCl+0.92CH_2Cl_2$: C, 60.49; H, 6.29; N, 7.32. Found: C, 60.04; H, 6.29; N, 7.08.

Example 1q

N-[3-(1-{[4-(4-methoxyphenylthio)phenyl]methyl}(4-piperidyl))$_4$-methyl phenyl]-2-methylpropanamide ESMS m/e: 489.2 (M+H)$^+$; Anal Calcd for $C_{30}H_{36}N_2O_2S+HCl+0.54CH_2Cl_2$: C, 64.24; H, 6.72; N, 4.91. Found: C, 64.25; H, 6.71; N, 4.82.

Example 1r 2-methyl-N-{4-methyl-3-[1-({4-[5-(trifluoromethyl)(2-pyridylthio)]phenyl} methyl)(4-piperidyl)]phenyl}propanamide ESMS m/e: 528.2 (M+H)$^+$.

Example 1s 2-methyl-N-(4-methyl-3-{1-[(4-phenylthiophenyl)methyl](4-piperidyl)}phenyl)propanamide ESMS m/e: 459.2 (M+H)$^+$; Anal Calcd for $C_{29}H_{34}N_2OS+HCl+0.35CH_2Cl_2$: C, 67.17; H, 6.86; N, 5.34. Found: C, 67.16; H, 6.93; N, 5.17.

Example 1t 2-methyl-N-(4-methyl-3-{1-[(4-(4-pyridylthio)phenyl)methyl](4-piperidyl)}phenyl)propanamide ESMS m/e: 460.2 (M+H)$^+$.

Example 1u

N-{3-[1-({4-[4-(tert-butyl)phenylthio]phenyl}methyl)(4-piperidyl)]-4-methyl phenyl}-2-methylpropanamide ESMS m/e: 515.3 (M+H)$^+$.

Example 1v

N-{5-[1-({4-[(4-chlorophenyl)sulfinyl]phenyl}methyl)(4-piperidyl)]-6-methyl(3-pyridyl)}cyclobutylcarboxamide ESMS m/e: 522.2 (M+H)$^+$.

Example 1w

N-{3-[1-({4-[(4-chlorophenyl)sulfinyl]phenyl}methyl)(4-piperidyl)]-4-methyl phenyl}-2-methylpropanamide ESMS m/e: 509.2 (M+H)$^+$.

Example 1x

N-{5-[1-({4-[(4-chlorophenyl)sulfonyl]phenyl}methyl)(4-piperidyl)]-6-methyl(3-pyridyl)}cyclobutylcarboxamide ESMS m/e: 538.2 (M+H)$^+$.

Example 1y

N-{5-[1-({4-[(4-chlorophenyl)sulfinyl]phenyl}methyl)(4-piperidyl)]-6-methyl(3-pyridyl)}methoxycarboxamide ESMS m/e: 498.2 (M+H)$^+$.

Example 1z

N-{5-[1-({4-[(4-chlorophenyl)sulfonyl]phenyl}methyl)(4-piperidyl)]-6-methyl(3-pyridyl)}methoxycarboxamide ESMS m/e: 514.2 (M+H)$^+$.

Example 1aa 2-(dimethylamino)-N-{3-[1-({4-[(4-chlorophenyl)sulfinyl]phenyl}methyl)(4-piperidyl)]-4-methylphenyl}acetamide ESMS m/e: 524.2 (M+H)$^+$.

Example 1bb

N-{3-[1-({4-[(4-chlorophenyl)sulfinyl]phenyl}methyl)(4-piperidyl)]-2,4,6-trifluorophenyl}-2-methylpropanamide ESMS m/e: 549.1 (M+H)$^+$.

Example 1cc

N-{3-[1-({3-chloro-4-[(4-chlorophenyl)sulfonyl]phenyl}methyl)(4-piperidyl)]4-methylphenyl}-2-methylpropanamide ESMS m/e: 559.0 (M+H)$^+$.

Example 1dd

N-{3-[1-({4-[(4-chlorophenyl)sulfonyl]-2-(trifluoromethyl)phenyl}methyl)(4-piperidyl)]-4-methylphenyl}-2-methylpropanamide ES-MS m/e: 593.0 (M+H)$^+$.

Example 1ee

Methoxy-N-[4-methyl-3-(1-{[4-(3-methylphenylthio)phenyl]methyl}(4-piperidyl))phenyl]carboxamide ESMS m/e: 461.4 (M+H)$^+$.

Example 1ff

N-[4-methyl-3-(1-{[4-(phenylsulfonyl)phenyl]methyl}(4-piperidyl))phenyl]acetamide ES-MS m/e: 463.4 (M+H)$^+$.

Example 1gg

N-{3-[1-({4-[(4-chlorophenyl)sulfonyl]phenyl}methyl)(4-piperidyl)]4-fluorophenyl}2-methylpropanamide ESMS m/e: 529.4 (M+H)$^+$.

Example 1hh

N-{3-[1-({4-[(3-chloro-4-fluorophenyl)sulfonyl]phenyl}methyl)(4-piperidyl)]4-methylphenyl}-2-methylpropanamide ESMS m/e: 543.0 (M+H)$^+$.

Example 1ii

N-{3-[1-({4-[(4-chlorophenyl)sulfonyl]phenyl}methyl)(4-piperidyl)]4-ethylphenyl}2-methylpropanamide ESMS m/e: 539.2 (M+H)$^+$.

Example 1jj

N-{3-[1-({4-[(4-chlorophenyl)sulfonyl]phenyl}methyl)(4-piperidyl)]-4-ethylphenyl}methoxycarboxamide ESMS m/e: 527.2 (M+H)$^+$.

Example 1kk

N-{3-[1-({4-[(4-chlorophenyl)sulfonyl]phenyl}methyl)(4-piperidyl)]-4-ethoxyphenyl}methoxycarboxamide ESMS m/e: 543.2 (M+H)$^+$.

Example 1ll

N-[3-(1-{[4-(4-chlorophenylthio)phenyl]methyl}(4-piperidyl))-4-methylphenyl]acetamide

ESMS: 465.4 (M+H)$^+$.

Example 1mm

N-{3-[1-({4-[(3,5-dichlorophenyl)sulfonyl]phenyl}methyl)(4-piperidyl)]-4-methylphenyl}methoxycarboxamide ESMS m/e: 547.3 (M+H)$^+$.

Example 1nn

Methoxy-N-(4-methyl-3-{1-[(6-(2-pyridylthio)(3-pyridyl))methyl](4-piperidyl)}phenyl)carboxamide ESMS m/e: 449.1 (M+H)$^+$.

Example 1oo

Methoxy-N-(4-methyl-3-{1-[(6-(4-pyridylthio)(3-pyridyl))methyl](4-piperidyl)}phenyl)carboxamide ESMS m/e: 448.9 (M+H)$^+$.

Example 1pp

N-[3-(1-{[6-(4-chlorophenylthio)(3-pyridyl)]methyl}(4-piperidyl))-4-fluorophenyl]methoxycarboxamide ESMS m/e: 486.0 (M+H)$^+$.

Example 1qq

N-[3-(1-{[6-(4-chlorophenylthio)(3-pyridyl)]methyl}(4-piperidyl))-4-methylphenyl]-2-methylpropanamide ESMS m/e: 494.0 (M+H)$^+$.

Example 1rr

N-[3-(1-{[6-(4-chlorophenylthio)(3-pyridyl)]methyl}(4-piperidyl))-4-methylphenyl]methoxycarboxamide ESMS m/e: 482.0 (M+H)$^+$.

Example 1ss

N-(4-fluoro-3-{1-[(6-(4-pyridylthio)(3-pyridyl))methyl](4-piperidyl)}phenyl)methoxycarboxamide ESMS m/e: 452.9 (M+H)$^+$.

Example 1tt 2-methyl-N-(4-methyl-3-{1-[(6-(4-pyridylthio)(3-pyridyl))methyl](4-piperidyl)}phenyl)propanamide ESMS m/e: 461.2 (M+H)$^+$.

Example 1uu 2-methyl-N-(4-methyl-3-{1-[(6-(2-pyridylthio)(3-pyridyl))methyl](4-piperidyl)}phenyl)propanamide ESMS m/e: 231.3 (M+2H)$^{2+}$/2.

Example 1vv 2-methyl-N-[4-methyl-3-(1-{[6-(2-pyridylsulfinyl)(3-pyridyl)]methyl}(4-piperidyl))phenyl]propanamide ESMS m/e: 477.0 (M+H)$^+$.

Example 1ww 3-(1-{[4-(4-chlorophenylthio)phenyl]methyl}(4-piperidyl))-4-methylphenylamine ESMS m/e: 423.2 (M+H)$^+$.

Example 1xx

1-[(4-{[4-(3-amino-6-methylphenyl)piperidyl]methyl}phenyl)sulfinyl]-4-chlorobenzene ESMS m/e: 439.2 (M+H)$^+$.

Example 1yy

4-[(4-{[4-(3-amino-6-methylphenyl)piperidyl]methyl}phenyl)sulfinyl]-1,2-difluorobenzene ESMS m/e: 441.2 (M+H)$^+$.

Example 1zz

1-[(4-{[4-(3-amino-6-methylphenyl)piperidyl]methyl}phenyl)sulfonyl]-3-fluorobenzene ESMS m/e: 439.2 (M+H)$^+$.

Example 1aaa

1-{[4-(3-amino-6-methylphenyl)piperidyl]methyl}-4-[(3,5-dimethylphenyl)sulfonyl]benzene ESMS m/e: 449.3 (M+H)$^+$.

Example 1bbb 3-(1-{[4-(3-chlorophenylthio)phenyl]methyl}(4-piperidyl))-4-methylphenylamine ESMS m/e: 423.2 (M+H)$^+$.

Example 1ccc

1-[(4-{[4-(3-amino-6-methylphenyl)piperidyl]methyl}phenyl)sulfinyl]-3-chlorobenzene ESMS m/e: 439.2 (M+H)$^+$.

Example 1ddd

4-[(4-{[4-(3-amino-6-methylphenyl)piperidyl]methyl}phenyl)sulfonyl]-2-chloro-1-fluorobenzene ESMS m/e: 473.1 (M+H)$^+$.

Example 1eee

4-[(4-{[4-(3-amino-6-methylphenyl)piperidyl]methyl}phenyl)sulfinyl]-2-chloro-1-fluorobenzene ESMS m/e: 457.1 (M+H)$^+$.

Example 2a

N-[3-(1-{[4-(4-methoxyphenylthio)phenyl]methyl}
(4-piperidyl))-4-methyl phenyl]-2-(methylamino)
acetamide To a stirred solution of 3-(1-{[4-(4-methoxyphenylthio)phenyl]methyl}(4-piperidyl))-4-methylphenylamine (121 mg, 0.289 mmol) in $CH_2Cl_2$/dimethylformamide (2.00/0.200 mL) was added 2-[(tert-butoxy)-N-methylcarbonylamino]acetic acid (54.6 mg, 0.289 mmol) and 1-[3-(dimethylamino)propyl]-3-ethylcarbodiimide hydrochloride (111 mg, 0.578 mmol) and 4-dimethylaminopyridine (5.00 mg). The reaction mixture was stirred at room temperature for 10 h, then partitioned between $CH_2Cl_2$ (10 mL) and saturated $NaHCO_3$ solution (10 mL) and the organic phase was separated and washed with water (10 mL), then brine (10 mL), dried over $MgSO_4$ and concentrated in vacuo to give the crude product. Purification by flash column chromatography (eluent: $CH_2Cl_2$ then 3% methanol in $CH_2Cl_2$) gave 2-[(tert-butoxy)-N-methylcarbonylamino]-N-[3-(1-{[4-(4-methoxyphenylthio)phenyl]methyl}(4-piperidyl))-4-methylphenyl]acetamide (84.7 mg, 50.1% yield) as a yellow solid.

2-[(tert-butoxy)-N-methylcarbonylamino]-N-[3-(1-{[4-(4-methoxyphenylthio)phenyl]methyl} (4-piperidyl))-4-methylphenyl]acetamide was dissolved in $CH_2Cl_2$ (1.00 mL) and trifluoroacetic acid (0.160 mL) was added to the stirred solution. Stirring was continued for 10 min then the reaction mixture was concentrated in vacuo to give a gum. The crude product was dissolved in saturated $NaHCO_3$ solution (10 mL to pH 10) and extracted with $CH_2Cl_2$ (2×10 mL). The combined organic layers were dried over $MgSO_4$ and concentrated in vacuo to give N-[3-(1-{[4-(4-methoxyphenylthio)phenyl]methyl}(4-piperidyl))-4-methylphenyl]2-(methylamino)acetamide (68.6 mg, 99.2% yield) as a yellow solid.

$^1H$ NMR ($CDCl_3$) δ 9.16 (s, 1H), 7.55-7.47 (m, 1H), 7.45-7.36 (m, 2H), 7.31-7.20 (m, 3H), 7.19-7.06 (m, 3H), 6.94-6.87 (m, 2H), 3.83 (s, 3H), 3.56 (s, 2H), 3.33 (s, 2H), 3.11-2.98 (m, 2H), 2.75-2.63 (m, 1H), 2.49 (s, 3H), 2.27 (s, 3H), 2.20-2.07 (m, 2H), 1.91-1.63 (m, 4H). ESMS m/e: 490.2 $(M+H)^+$.

The following intermediates were prepared analogously:

Example 2b ((2S)(2-piperidyl))-N-[3-(1-{[4-(4-methoxyphenylthio)phenyl]methyl}(4-piperidyl))-4-methylphenyl]carboxamide ESMS m/e: 530.3 $(M+H)^+$.

Example 2c

N-[3-(1-{[4-(4-methoxyphenylthio)phenyl]methyl}
(4-piperidyl))-4-methyl phenyl]-4-piperidylcarboxamide ESMS m/e: 530.3 $(M+H)^+$.

Example 2d

N-[3-(1-{[4-(3,4-difluorophenylthio)phenyl]methyl}
(4-piperidyl))-4-methyl phenyl]-2-(methylamino)
acetamide ESMS m/e: 496.2 $(M+H)^+$.

Example 2e ((2S)(2-piperidyl))-N-[3-(1-{[4-(3,4-difluorophenylthio)phenyl]methyl}(4-piperidyl))-4-methylphenyl]carboxamide ESMS m/e: 536.3 $(M+H)^+$.

Example 2f

N-[3-(1-{[4-(3,4-difluorophenylthio)phenyl]methyl}
(4-piperidyl))-4-methyl phenyl]4-piperidylcarboxamide ESMS m/e: 536.2 $(M+H)^+$.

Example 2g 2-(methylamino)-N-(4-methyl-3-{1-[(4-(2-pyridylthio)phenyl)methyl](4-piperidyl)}phenyl)acetamide ESMS m/e: 461.2 $(M+H)^+$.

Example 2h

N-(4-methyl-3-{1-[(4-(2-pyridylthio)phenyl)methyl]
(4-piperidyl)}phenyl)-4-piperidylcarboxamide ESMS m/e: 501.2 $(M+H)^+$.

Example 2i ((2S)(2-piperidyl))-N-(4-methyl-3-{1-[(4-(2-pyridylthio)phenyl)methyl](4-piperidyl)}phenyl)carboxamide ESMS m/e: 501.2 $(M+H)^+$.

Example 2j

N-[3-(1-{[4-(4-chlorophenylthio)phenyl]methyl}(4-piperidyl))-4-methylphenyl]-2-(ethylamino)acetamide ESMS m/e: 508.2 $(M+H)^+$.

Example 2k ((2R)(2-piperidyl))-N-[3-(1-{[4-(4-chlorophenylthio)
phenyl]methyl}(4-piperidyl))-4-methylphenyl]carboxamide ESMS m/e: 534.2 $(M+H)^+$.

Example 2l

N-[3-(1-{[4-(4-chlorophenylthio)phenyl]methyl}(4-piperidyl))-4-methylphenyl]2-(methylamino)acetamide ESMS m/e: 494.2 $(M+H)^+$.

Example 2m

N-[3-(1-{[4-(4-chlorophenylthio)phenyl]methyl}(4-piperidyl))-4-methylphenyl]4-piperidylcarboxamide ESMS m/e: 534.2 (M+H)$^+$.

Example 2n

N-{3-[1-({4-[(4-chlorophenyl)sulfinyl]phenyl}methyl)(4-piperidyl)]-4-methyl phenyl}-2-(methylamino)acetamide ESMS m/e: 510.3 (M+H)$^+$.

Example 2o

N-{3-[1-({4-[(4-chlorophenyl)sulfonyl]phenyl}methyl)(4-piperidyl)]-4-methylphenyl}2-(ethylamino)acetamide ESMS m/e: 540.2 (M+H)$^+$.

Example 2p

N-{3-[1-({4-[(4-chlorophenyl)sulfonyl]phenyl}methyl)(4-piperidyl)]-4-methyl phenyl}-2-(methylamino)acetamide ESMS m/e: 526.1 (M+H)$^+$.

Example 2q

N-{3-[1-({4-[(4-chlorophenyl)sulfonyl]phenyl}methyl)(4-piperidyl)]-4-methylphenyl}4-piperidylcarboxamide ESMS m/e: 566.2 (M+H)$^+$.

Example 2r

N-[3-(1-{[6-(4-chlorophenylthio)(3-pyridyl)]methyl}(4-piperidyl))-4-methylphenyl]2-(methylamino)acetamide ESMS m/e: 495.2 (M+H)$^+$.

Example 2s 2-(methylamino)-N-[4-methyl-3-(1-{[6-(4-methylphenylthio)(3-pyridyl)]methyl}(4-piperidyl))phenyl]acetamide ESMS m/e: 475.3 (M+H)$^+$.

Example 2t

N-[3-(1-{[6-(2-chlorophenylthio)(3-pyridyl)]methyl}(4-piperidyl))-4-methylphenyl]2-(methylamino)acetamide ESMS m/e: 495.2 (M+H)$^+$.

Example 3a

Cyclopropyl-N-{4-methyl-3-[1-({4-[(4-methylphenyl)sulfinyl]phenyl}methyl)(4-piperidyl)]phenyl}carboxamide Into a vial was added 4-(bromomethyl)-1-[(4-methylphenyl)sulfinyl]benzene (100 mg, 0.320 mmol), cyclopropyl-N-(4-methyl-3-(4-piperidyl)phenyl)carboxamide (50.0 mg, 0.190 mmol), potassium carbonate (60.0 mg, 0.430 mmol), NaI (30.0 mg, 0.200 mmol) and 2.50 mL of dimethylformamide. The mixture was stirred for 2-3 min at 25° C. and heated to 90° C. (oil bath). After stirring 12 h at 90° C., the mixture was allowed to cool to 25° C. and was diluted with 50 mL of EtOAc. The reaction solution was then washed with water (3×30 mL) and the aqueous solution was extracted with 30 mL of EtOAc. The organic solutions were combined and dried over MgSO$_4$. Removal of solvent in vacuo gave crude product that was purified by flash column chromatography (eluent: 97% EtOAc: 3% methanol (2 M ammonia)) to afford cyclopropyl-N-{4-methyl-3-[1-({4-[(4-methylphenyl)sulfinyl]phenyl}methyl)(4-piperidyl)]phenyl}carboxamide (36.0 mg, 39.1% yield). $^1$H NMR (CDCl$_3$) δ 7.62 (s, 1H), 7.54-7.43 (m, 4H), 7.42-7.31 (m, 3H), 7.24-7.10 (m, 3H), 7.05-6.91 (m, 1H), 3.47 (s, 2H), 2.92-2.81 (m, 2H), 2.66-2.52 (m, 1H), 2.29 (s, 3H), 2.18 (s, 3H), 2.08-1.97 (m, 2H), 1.76-1.54 (m, 4H), 1.48-1.38 (m, 1H), 1.02-0.91 (m, 2H), 0.75-0.68 (m, 2H). ESMS m/e: 487.2 (M+H)$^+$.

The following compounds were prepared analogously:

Example 3b 2-methyl-N-[4-methyl-3-(1-{[4-(phenylsulfonyl)phenyl]methyl}(4-piperidyl)) phenyl]propanamide ESMS m/e: 491.2 (M+H)$^+$.

Example 3c

N-[4-chloro-3-(1-{[4-(phenylsulfonyl)phenyl]methyl}(4-piperidyl))phenyl]2-methylpropanamide ESMS m/e: 511.2 (M+H)$^+$.

Example 3d

N-{5-[1-({4-[(4-chlorophenyl)sulfonyl]phenyl}methyl)(4-piperidyl)]-2-fluoro-4-methylphenyl}-2-methylpropanamide ESMS m/e: 543.2 (M+H)$^+$.

Example 3e

Cyclopropyl-N-[2-fluoro-4-methyl-5-(1-{[4-(phenylsulfonyl)phenyl]methyl}(4-piperidyl))phenyl]carboxamide ESMS m/e: 507.2 (M+H)$^+$.

Example 3f

Cyclopropyl-N-{3-[1-({4-[(4-fluorophenyl)sulfonyl]phenyl}methyl)(4-piperidyl)]-4-methylphenyl}carboxamide ESMS m/e: 507.3 (M+H)+.

Example 3g

N-{3-[1-({4-[(4-chlorophenyl)sulfonyl]phenyl}methyl)(4-piperidyl)]4-methyl phenyl}-2-methylpropanamide ESMS m/e: 525.2 (M+H)+.

Example 4a 3-(1-{[4-(4-methoxyphenylthio)phenyl]methyl}(4-piperidyl))-4-methylphenylamine N-[3-(1-{[4-(4-methoxyphenylthio)phenyl]methyl}(4-piperidyl))-4-methylphenyl](phenylmethoxy)carboxamide (486 mg, 0.881 mmol) was dissolved in methanol (10.0 mL) and an aqueous KOH solution (40%, 1.20 mL) was added. The reaction mixture was heated at 100° C. for 10 h. After cooling to room temperature, the reaction mixture was poured into a separatory funnel. The phases were separated and the aqueous phase was extracted with $CH_2Cl_2$ (2×20 mL). The combined organic layers were washed with brine, dried over $Na_2SO_4$, filtered and concentrated in vacuo. Purification by flash column chromatography (eluent: Hexane:EtOAc (1:1 then 1:4)) gave the desired product (362 mg, 98.2% yield). $^1$H NMR ($CDCl_3$) δ 7.43-7.35 (m, 4H), 7.24-7.11 (m, 3H), 6.93-6.85 (m, 2H), 6.63-6.58 (m, 1H), 6.48-6.42 (m, 1H), 3.82 (s, 3H), 3.48 (s, 2H), 3.03-2.91 (m, 2H), 2.68-2.54 (m, 1H), 2.20 (s, 3H), 2.13-1.98 (m, 2H), 1.79-1.64 (m, 4H). ESMS m/e: 419.2 (M+H)+.

The following compounds were prepared analogously:

Example 4b

1-[(4-{[4-(3-amino-6-methylphenyl)piperidyl]methyl}phenyl)sulfonyl]-4-chlorobenzene ESMS m/e: 455.2 (M+H)+.

Example 4c 3-(1-{[4-(3,4-difluorophenylthio)phenyl]methyl}(4-piperidyl))-4-methylphenylamine ESMS m/e: 425.2 (M+H)+.

Example 4d 4-methyl-3-{1-[(4-(2-pyridylthio)phenyl)methyl](4-piperidyl)}phenylamine ESMS m/e: 390.2 (M+H)+.

Example 4e 4-methyl-3-(1-{[4-(4-methylphenylthio)phenyl]methyl}(4-piperidyl))phenylamine ESMS m/e: 403.2 (M+H)+.

Example 4f

4-{[4-(3-amino-6-methylphenyl)piperidyl]methyl}-1-[(4-methylphenyl)sulfonyl]benzene ESMS m/e: 435.1 (M+H)+.

Example 4g

4-[(4-{[4-(3-amino-6-methylphenyl)piperidyl]methyl}phenyl)sulfonyl]-1,2-difluorobenzene ESMS m/e: 457.2 (M+H)+.

Example 4h

4-{[4-(3-amino-6-methylphenyl)piperidyl]methyl}-1-(phenylsulfonyl)benzene

ESMS m/e: 421.1 (M+H)+.

Example 4i 4-methyl-3-{1-[(4-phenylthiophenyl)methyl](4-piperidyl)}phenylamine ESMS m/e: 389.3 (M+H)+.

Formulations

The pharmaceutical formulations of the invention may be prepared by conventional methods in the art.

For example tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatine, lactose, gums, and the like. Any other adjuvants or additives usually used for such purposes such as colorings, flavorings, preservatives etc. may be used provided that they are compatible with the active ingredients.

1) Tablets Containing 5.0 mg of Compound 1k Calculated as the Free Base:

| | |
|---|---|
| Compound 1k | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets Containing 0.5 mg of Compound 1k Calculated as the Free Base:

| | |
|---|---|
| Compound 1k | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup Containing 25 mg of Compound 1k per Milliliter:

| | | |
|---|---|---|
| Compound 1k | 25 mg | |
| Sorbitol | 500 mg | |
| Hydroxypropylcellulose | 15 mg | |
| Glycerol | 50 mg | |
| Methyl-paraben | 1 mg | |
| Propyl-paraben | 0.1 mg | |
| Ethanol | 0.005 mL | |
| Flavor | 0.05 mg | |
| Saccharin | 0.5 mg | |
| Water | 1 mL | |

In Vitro Methods

The pharmacological properties of the compounds of the present invention were evaluated at the cloned rat MCH1 receptor using the protocols disclosed in U.S. Pat. No. 6,727,264, the contents of which are hereby incorporated by reference.

Using this protocol, the inhibition by the compound of the binding of a radiolabeled ligand (tritiated SNAP-7941) to membranes harvested from CHO cells expressing cloned rat MCH1 receptors was determined in vitro. The radiochemical synthesis of tritiated SNAP-7941 was performed by Amersham Pharmacia Biotech, Cardiff, Wales.

Briefly, the affinity of the compounds was measured by their ability to displace tritiated SNAP-7941 from rat MCH1 expressing membranes. The compound and radioligand were incubated with the membranes at 25° C. for 90 min. Incubation was terminated by rapid vacuum filtration over GF/C glass fiber filters, presoaked in 5% PEI using 50 nM Tris pH 7.4 as wash buffer. In all experiments, nonspecific binding was defined using 10 pM of tritiated SNAP-7941.

The binding affinities for the compounds in the present invention, exemplified above, at the MCH1 receptor were determined to be 200 nM or less. For the majority of the compounds, the Ki values are 100 nM or less, and for a large group of compounds the Ki values are 10 nM or less.

What is claimed is:

1. A compound having the structure:

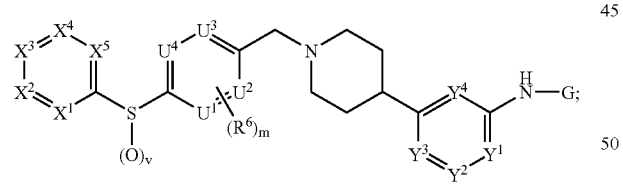

wherein each $X^1$, $X^2$, $X^3$, $X^4$ and $X^5$ is independently $CR^1$;

wherein each $U^1$, $U^2$, $U^3$ and $U^4$ is independently CH;

wherein each $Y^1$, $Y^3$ and $Y^4$ is independently $CR^7$, and $Y^2$ is N;

wherein G is hydrogen or —C(O)D;

wherein D is

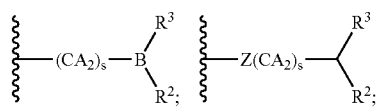

-continued

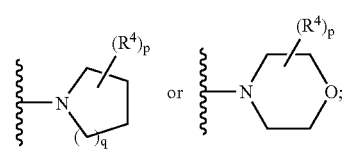

wherein Z is —N($R^5$) or —O—;

wherein each A is independently H or straight chained or branched $C_1$-$C_4$ alkyl;

wherein B is CH or N;

wherein each $R^1$ is independently H, straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein $R^2$ is H or straight chained or branched $C_1$-$C_4$ alkyl;

wherein $R^3$ is H or straight chained or branched $C_1$-$C_4$ alkyl;

or wherein if B is N, then the $R^2$ moiety, B, the $R^3$ moiety and a bond formed between the $R^2$ moiety and the $R^3$ moiety form:

or wherein if B is CH, then the $R^2$ moiety, B, the $R^3$ moiety and a bond formed between the $R^2$ moiety and the $R^3$ moiety form cyclopropyl, cyclobutyl, cyclopentyl or cyclohexyl;

wherein $R^4$ is H, straight chained or branched $C_1$-$C_4$ alkyl, straight chained or branched $C_1$-$C_4$ fluoroalkyl or F;

wherein $R^5$ is H or straight chained or branched $C_1$-$C_4$ alkyl;

wherein each $R^6$ is independently straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein each $R^7$ is independently H, straight chained or branched $C_1$-$C_7$ alkyl, straight chained or branched $C_1$-$C_7$ fluoroalkyl, straight chained or branched $C_1$-$C_7$ alkoxy, F, Cl, Br or I;

wherein $R^8$ is H, straight chained or branched $C_1$-$C_4$ alkyl, straight chained or branched $C_1$-$C_4$ fluoroalkyl or F;

wherein m is an integer from 0 to 4 inclusive;

wherein n is an integer from 0 to 2 inclusive;

wherein p is an integer from 0 to 4 inclusive;

wherein q is an integer from 0 to 3 inclusive;

wherein r is 1 or 2;

wherein s is an integer from 0 to 4 inclusive;

wherein t is an integer from 2 to 4 inclusive;

wherein v is an integer from 0 to 2 inclusive; and wherein w is an integer from 1 to 5 inclusive;

or a pharmaceutically acceptable salt thereof.

2. The compound of claim 1, having the structure:

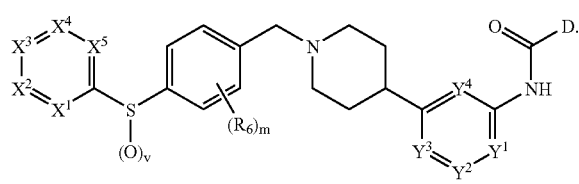

3. The compound of claim 2, wherein m is 0 or 1 and $R^6$ is methyl, F or Cl.

4. The compound of claim 1, wherein each $U^1$, $U^2$, $U^3$ and $U^4$ is CH; and G is hydrogen.

5. The compound of claim 4, wherein m is 0 or 1 and $R^6$ is methyl, F or Cl.

6. A pharmaceutical composition comprising a therapeutically amount of a compound of claim 1 and a pharmaceutically acceptable carrier.

7. A process for making a pharmaceutical composition comprising mixing a therapeutically amount of a compound of claim 1 and a pharmaceutically acceptable carrier.

8. The compound of claim 3, wherein each $R^1$ is independently H, methyl, F or Cl, and each $R^7$ is independently H, F or methyl.

9. The compound of claim 8, wherein D is

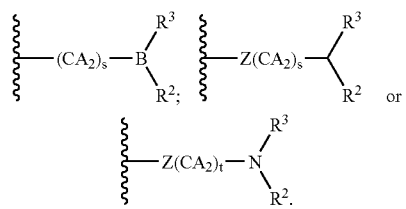

10. The compound of claim 9, wherein D is

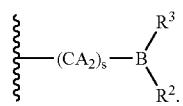

11. The compound of claim 10, wherein B is N, then the $R^2$ moiety, B, the $R^3$ moiety and the bond formed between the $R^2$ moiety and the $R^3$ moiety form:

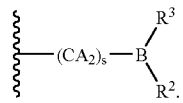

or wherein B is CH then the $R^2$ moiety, B, the $R^3$ moiety and the bond formed between the $R^2$ moiety and the $R^3$ form cyclopropyl, cyclobutyl, cyclopentyl or cyclohexyl.

12. The compound of claim 10, wherein B is N, and $R^2$ and $R^3$ each are independently H, methyl or ethyl.

13. The compound of claim 12, wherein s is 1 or 2.

14. The compound of claim 10, wherein $R^2$ and $R^3$ are each independently H, methyl or ethyl and B is CH.

15. The compound of claim 14, wherein each A is independently H, methyl or ethyl;
s is 0 or 1; and m is 0.

16. The compound of claim 9, wherein D is

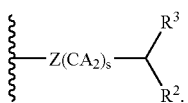

17. The compound of claim 16, wherein each A is independently H, methyl or ethyl;
Z is O; s is 0 or 1; and m is 0.

18. The compound of claim 17, wherein $R^2$ and $R^3$ are independently H, methyl or ethyl.

19. The compound of claim 9, wherein D is

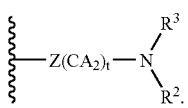

20. The compound of claim 19, wherein the $R^2$ moiety, N, the $R^3$ moiety and the bond formed between the $R^2$ moiety and the $R^3$ moiety form:

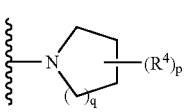

21. The compound of claim 19, wherein $R^2$ and $R^3$ are each independently H, methyl or ethyl.

* * * * *